United States Patent
Chabriere et al.

(10) Patent No.: US 8,372,618 B2
(45) Date of Patent: Feb. 12, 2013

(54) MUTATED HYPERTHERMOPHILIC PHOSPHOTRIESTERASES AND THEIR USES

(75) Inventors: Eric Chabriere, Marseilles (FR); Mickael Elias, Florange (FR)

(73) Assignees: Universite Henri Poincare Nancy 1, Nancy (FR); Centre National de la Recherche Scientifique, Paris (FR)

( * ) Notice: Subject to any disclaimer, the term of this patent is extended or adjusted under 35 U.S.C. 154(b) by 316 days.

(21) Appl. No.: 12/597,847

(22) PCT Filed: Apr. 25, 2008

(86) PCT No.: PCT/FR2008/000596
§ 371 (c)(1),
(2), (4) Date: Mar. 24, 2010

(87) PCT Pub. No.: WO2008/145865
PCT Pub. Date: Dec. 4, 2008

(65) Prior Publication Data
US 2010/0333221 A1  Dec. 30, 2010

(30) Foreign Application Priority Data

Apr. 27, 2007 (FR) ..................................... 07 03104

(51) Int. Cl.
C12N 11/00 (2006.01)
C12N 9/00 (2006.01)
C12N 9/14 (2006.01)
C12N 1/20 (2006.01)
C07H 21/04 (2006.01)

(52) U.S. Cl. ..... 435/195; 435/174; 435/183; 435/252.3; 536/23.2

(58) Field of Classification Search ........................ None
See application file for complete search history.

(56) References Cited

FOREIGN PATENT DOCUMENTS
WO   2005/059125   6/2005

OTHER PUBLICATIONS

Elias et al. J Mol Biol. Jun. 20, 2008;379(5):1017-28. Epub Apr. 16, 2008.*
Accession Q97VT. Oct. 1, 2001.*
Merone et al. Extremophiles. Aug. 2005;9(4):297-305. Epub May 21, 2005.*
Afriat et al. Biochemistry. Nov. 21, 2006;45(46):13677-86.*
Elias Mikael et al: "Crystallization and preliminary X-ray diffraction analysis of the hyperthermophilic *Sulfolobus solfataricus* phosphotriesterase." ACTA Crystallographica. Section F, Structural Biology and Crystallization Communications Jul. 1, 2007, vol. 63, No. Pt 7, pp. 553-555, XP009089597 ISSN: 1744-3091 the whole document.
Porzio et al: "A new phosphotriesterase from *Sulfolobus acidocaldarius* and its comparison with the homologue from *Sulfolobus solfataricus*" Biochimie, Masson, Paris, FR, vol. 89, No. 5, Jan. 27, 2007, pp. 625-636, XP022081069 1SSN: 0300-9084 figures 2,3 (An Abstract is provided in English).
Merone Luigia et al: "A thermostable phosphotriesterase from the archaeon *Sulfolobus solfataricus*: cloning, overexpression and properties" EXTREMOPHILES, vol. 9, No. 4, Aug. 2005, pp. 297-305, XP002451459 ISSN: 1431-0651 figure 1 (An Abstract is provided in English).
International Search Report dated Nov. 12, 2008, in PCT application.

* cited by examiner

*Primary Examiner* — Christian Fronda
(74) *Attorney, Agent, or Firm* — Young & Thompson

(57) ABSTRACT

A subject of the present invention is mutated hyperthermophilic phosphotriesterases (PTEs) possessing a lactonase activity, and their uses as bioscavengers within the context of the decontamination of the surfaces of materials, of the skin or mucous membranes, contaminated with organophosphorus compounds, or within the context of the preparation of medicaments which can be used within the context of the prevention or treatment of an external contamination or of an internal poisoning by ingestion or inhalation by organophosphorus compounds, or within the context of the pollution control of water polluted with organophosphorus compounds.

35 Claims, No Drawings

MUTATED HYPERTHERMOPHILIC PHOSPHOTRIESTERASES AND THEIR USES

FIELD OF THE INVENTION

A subject of the present invention is mutated hyperthermophilic phosphotriesterases (PTEs), and their uses as bioscavengers within the context of the decontamination of the surfaces of materials, of the skin or mucous membranes, contaminated with organophosphorus compounds, or within the context of the preparation of garments, gloves, cartridges, organophosphorus scavengers, or within the context of the preparation of medicaments which can be used within the context of the prevention or treatment of an external contamination or of an internal poisoning by ingestion or inhalation of organophosphorus compounds, or within the context of the pollution control of water polluted with organophosphorus compounds, as well as the nucleotide sequences encoding for these mutated hyperthermophilic PTEs and their use within the context of the preparation of bacteria expressing these PTEs, in particular at their surface.

BACKGROUND OF THE INVENTION

Organophosphorus Compounds

The organophosphorus compounds (OPs) are highly toxic molecules which make up certain chemical warfare agents and pesticides. Some of these compounds such as paraoxon or parathion are used for their insecticidal property. In fact, they are easy to manufacture and are widely used for agriculture in developing countries. Unfortunately, this very widespread use is responsible for large numbers of cases of poisoning world-wide (200,000 deaths per year according to the WHO).

Most OPs are unstable products as they hydrolyze rapidly. They do not therefore persist in the environment in their toxic form. By contrast, certain products developed by armies are much more stable and dangerous, such as sarin, soman, tabun or VX. These chemical warfare agents are now of increasing interest to terrorists. Sarin in particular has already been used during attacks carried out by the Aum sect, in 1994 at Matsumoto and in 1995 in the Tokyo metro. Faced with these growing threats, the study and especially the development of effective means of decontamination has never been more urgent.

The organophosphorus compounds act by percutaneous absorption and by inhalation. They are very often colourless and odourless liquids. Poisoning with one of these agents rapidly becomes apparent (less than 1 minute to 60 minutes) due to characteristic and extremely serious symptoms (even the death of the poisoned subject). These molecules, once ingested into the human organism, have a neurotoxic effect. They attack an enzyme which is very important for the proper functioning of the nervous system: acetylcholinesterase. This enzyme is essential in the transmission of nerve messages. In fact, as the impulse passes from neuron to neuron, the electrical information is converted to a chemical message in the synaptic cleft. The molecules thus released are called neurotransmitter (for example: acetylcholine). Once released in the cleft, the acetylcholine mostly binds to the receptors of the post-synaptic neuron in order to ensure the continuity of the nerve message. The bound and non-bound molecules must then be re-trapped or degraded, thus allowing the regulation of the intensity and duration of the impulse. The role of the acetylcholinesterases is therefore to ensure that the nerve message stops, by degrading the acetylcholine in the synaptic cleft.

The OPs react rapidly with the serine at the active site of the acetylcholinesterases, forming an inactive phosphoenzyme. The covalent intermediate thus formed, the enzyme has lost all activity. These compounds therefore constitute irreversible inhibitors of these enzymes. The acetylcholine is then no longer degraded in the synaptic cleft and accumulates.

In order to be prepared for these dangers, prevention and decontamination protocols are provided. At present equipment is decontaminated using highly concentrated soda (NaOH). Protective suits and masks have been designed to prevent all contact with these agents. In case of the poisoning of humans, treatment with soda obviously cannot be envisaged. The victim is simply decontaminated using a solution of sodium hypochlorite (Javel water) and washed with copious amounts of soap and water. Foulon gloves also allow the liquid to be absorbed by the victim's skin. For cases of inhalation (percutaneous or not percutaneous) of neurotoxic agents, there is pretreatment with pyrostigmine, which can be taken in cachet form. This molecule reversibly blocks the acetylcholinesterases and prevents the OPs from binding to them. The individual's life is thus saved. Moreover, an emergency treatment of symptoms also exists in the form of self-injection syringes containing atropine (anticholinergic), diazepam (anticonvulsant) and pralidoxime (reactivator of the inhibited acetylcholinesterases). The injection must however be given immediately after poisoning in order to be effective. This does not however prevent the appearance of incapacitating sequelae.

Although some progress in prophylaxia has been made with the abovementioned techniques in the last twenty years, the treatments for these poisonings and existing protection nevertheless remain unsatisfactory. Unfortunately, all the pharmacological leads explored seem to come to an impasse. However, the emergence of the concept of a "bioscavenger" has given rise to new hopes of a more effective armamentarium. In fact, the idea of using enzymes capable of trapping and/or degrading the OPs on the skin and in the blood before they reach their neuromuscular and central biological targets is particularly attractive.

Human ButyrylCholinesterase (BuChe) is an enzyme similar to acetylcholinesterase, the physiological role of which is not clearly established. Despite that, it represents great hope as it traps the organophosphorus compounds in the blood route before they reach their targets (Raveh et al., 1993). Furthermore, the natural enzyme injected into humans is particularly stable, with a half-life of 11 days. However, this natural scavenger is in much too low a quantity in the blood to protect us naturally from the dangers of the OPs. In fact it acts as a stoichiometric binder of the OPs: one enzyme can only neutralize a single molecule. A rapid calculation makes it possible to show that huge quantities of enzyme are needed in order to obtain an effective treatment. The resources to be used then seem disproportionate and would correspond to a dose of 200 mg of protein per injection and per soldier. However, for want of something better, BuChE represents a concrete plan in particular for the American army which, at the end of 2006, provided for a million doses to be made available for its soldiers. The production of the enzyme is ensured by genetic engineering thanks to transgenic goats. The need for such a quantity of protein is nevertheless very expensive, and despite the resources utilized, this enterprise constitutes a major technological challenge. A few variants of BuChE having an OP-hydrolase activity do exist but their catalysis is very slow in comparison with enzymes capable of hydrolyzing the OPs naturally.

Human paraoxonase (HPON1) is an OP-hydrolase which has numerous advantages. Its protective role against OP poisoning has been established in mice. Furthermore, its human origin should avoid multiple injections of the therapeutic protocols inducing an immune response. HPON1 is a plasma protein mainly associated with HDL. The three-dimensional structure of the natural enzyme has not been resolved, only the structure of a human-mouse-rat-rabbit chimera of PON1, (Harel et al., 2004). Nevertheless, this structure has not made it possible to obtain more active mutants. Furthermore, a pharmacological use is impossible in the immediate future. In fact, all attempts to obtain a large quantity of active human paraoxonase have failed for technical reasons.

Other promising OP-hydrolases have been isolated. These are enzymes of the family of the phosphotriesterases (PTEs). These enzymes constitute true catalytic scavengers discovered in soil bacteria: in particular *Pseudomonas diminuta* and *flavobacterium* sp. (Munnecke, 1976) for the opd gene, and *Agrobacterium radiobacter* for the opdA gene (Jackson et al., 2005). The PTEs are enzymes which are extremely promising for the development of a bioscavenger for neurotoxic agents. But there are also fundamental concerns about these enzymes: in fact, the biological implication(s) (s) of the latter remain completely unknown. Furthermore, the catalytic mechanism of these extremely effective enzymes is somewhat obscure.

The PTEs are the most active of the enzymes known to degrade the OPs. Studying these could make it possible to carry out treatments for therapeutic (cutaneous and opthalmological) decontaminations which would advantageously replace the only existing effective means which is soda. The latter obviously cannot be used on living beings. Moreover, the PTEs would also be effective for decontaminating soil polluted with pesticides. They could also be used for detecting OP pollution. Thus, there are projects which attempt to chemically bind these proteins to a support and detect any catalysis by various means such as the detection of electric signals or by spectrophotometry. Another major asset is that the PTEs are capable of hydrolyzing a broad spectrum of OPs, such as parathion, paraoxon, soman, sarin and the most toxic of all, VX.

The hypotheses relating to the origin of this OP-hydrolase activity in bacteria are multiple and controversial, even though it seems more likely that this activity results from a structural similarity of its natural substrate to these poisons. Moreover, the physiological role of these enzymes remains unknown (Aubert et al., 2004). Several genes exist which are known to encode for mesophilic PTEs. A first gene (opd) was simultaneously isolated from *P. diminuta* and *Flavobacterium* sp., and encodes a protein of 365 amino acids. This protein possesses a peptide signal of 29 residues allowing its addressing in the periplasmic space. Another known gene (opda), isolated from *A. radiobacter* (Jackson et al., 2005), encodes a protein of 362 amino acids possessing a peptide signal of 33 residues. These two proteins share 90% sequence identity. Whilst these mesophilic PTEs are very active vis-à-vis the OPs, they are however expensive to produce, and unstable.

Recently, a novel protein of this family was isolated and purified (Merone et al., 2005). This metalloenzyme of 35.5 kDa possesses 31% sequence identity with the PTEs of *P. diminuta* and was isolated from the archaeon *Sulfolobus solfataricus*. This organism lives in extreme conditions (87°-93° C. and pH 3.5-5). The latter confer exceptional thermostability properties upon this protein. This is a hyperthermophilic enzyme the maximum activity of which occurs at approximately 95° C., and it is clearly less active vis-à-vis paraoxon than the PTEs of *P. diminuta*. Another hyperthermophilic PTE has been isolated from *Sulfolobus acidocaldarius* (Porzio et al., 2007). The hyperthermophilic PTEs are less active vis-à-vis the OPs than the mesophilic PTEs, but on the other hand have the advantage of being very stable and inexpensive to produce.

Bacterial Infections

Bacterial infections constitute one of the major causes of human pathologies. Some of these infections can be contracted in hospital and constitute a major public health problem. In France, according to the different studies carried out, approximately 5 to 10% of hospitalized individuals fall victim during their stay in hospital, i.e. 600,000 to 1,000,000 patients per year. On top of the pathologies initially responsible for the hospitalization, these infections aggravate the patients' vital prognosis (approximately 6000 deaths per year, the tenth cause of deaths in France). Besides this fact there is also the additional financial cost of prolonged stays in hospital and the provision of expensive treatment. These problems are further exacerbated by the appearance of a growing number of cases of antibiotic resistance. A certain number of strategies are being developed in order to acquire new tools against this resistance. One of the most promising leads involves disturbing communications between bacteria. In fact, although bacteria are single-cell organisms, they are capable of communicating with each other and thus responding collectively to an environmental change. These communication mechanisms, known as "quorum sensing" (QS), allow the synchronization and modulations of the expression of certain genes (Federle and Bassler, 2003; Fuqua and Greenberg, 2002; Whitehead et al., 2001). This communication is modulated by small "signal" molecules, capable of freely diffusing through the cell membranes and regulating the expression profiles of genes. Moreover, the QS phenomenon is not limited to the prokaryotes, since certain single-cell eukaryotic pathogens of algae also use QS for coordinating certain biological functions, such as virulence (Oh et al., 2001).

Of all the signals used for QS, the acyl homoserine lactones (AHLs) appear to be the most widespread (in particular in Gram-negative bacteria) and are the most studied.

Their involvement is demonstrated in numerous significant biological functions, such as symbiosis, conjugation, production of antibiotics, sporulation, virulence and biofilm formation (Fuqua and Greenberg, 2002; Whitehead et al., 2001; Zhang, 2003).

The concentration of these "signal" molecules is very significant and regulated in part by enzymes capable of degrading these compounds. In particular there are AHL acylases and AHL lactonases which are capable of degrading these lactones, such as AiiA, originating from *Bacillus thuringiensis* (Dong et al., 2002). In order to combat bacterial infections, the idea of disturbing quorum sensing is an extremely promising lead (Rasmussen and Givskov, 2006). In fact, given that QS mutant pathogens no longer express virulence genes and become non-virulent (Passador et al., 1993; Pirhonen et al., 1993), it therefore seems possible to control bacterial infections by attenuating the QS of pathogens.

Thus, the expression of a QS-attenuating enzyme: a "quorum quenching" (QQ) enzyme, whether this is an AHL lactonase or an AHL acylase, in plant or human pathogens such as *Erwinia carotovora* and *Pseudomonas aeruginosa*, significantly reduces their virulence (Dong et al., 2000; Lin et al., 2003; Reimmann et al., 2002). Furthermore, transgenic plants expressing a QQ lactonase are effectively resistant to pathogen infections (Dong et al., 2001).

Recently, the protein SsoPox, originating from the hyperthermophilic archaeon *Sulfolobus solfataricus* has been cloned and characterized for its phosphotriesterase activity (Merone et al., 2005). This protein is hyperthermostable with a denaturation half-life of approximately 4 hours at 90 to 95 and 100° C., respectively. This allows very effective and low-cost purification of the recombinant protein by heating the cell lysates, and thus precipitating the host proteins (*Escherichia coli*). In 2006, it was shown that SsoPox possesses significant AHL lactonase activity (Afriat et al., 2006).

SUMMARY OF THE INVENTION

The purpose of the present invention is essentially to provide novel PTEs having the advantage of being both:
more active vis-à-vis the OPs than the abovementioned wild-type hyperthermophilic PTEs,
more stable and less expensive to produce than the abovementioned wild-type mesophilic PTEs.

A purpose of the invention is also to provide new bioscavenging compounds which can be used within the context of the decontamination of the surfaces of materials, of the skin or mucous membranes, contaminated with organophosphorus compounds, or within the context of the preparation of medicaments which can be used within the context of the prevention or treatment of an external contamination or of an internal poisoning by ingestion or inhalation of organophosphorus compounds, or within the context of the pollution control of water polluted with organophosphorus compounds.

Another purpose of the present invention is to provide kits for the decontamination of the surfaces of materials, of the skin or mucous membranes, contaminated with organophosphorus compounds, or for the pollution control of water polluted with organophosphorus compounds, or for the destruction of stocks of neurotoxic agents.

Another purpose of the present invention is to provide a scavenger for these organophosphorus compounds, having the advantage of being extremely sensitive thanks to the abovementioned capabilities of the novel PTEs.

Another purpose of the present invention is to provide materials impregnated with novel PTEs having the abovementioned advantages, in liquid or solid form, such as gloves, various garments (in particular fixing to fabrics for chemical protection suits), wipes, spray foams.

Another purpose of the present invention is to provide pharmaceutical compositions, in particular in injectable form or in the form of ointments, comprising the novel PTEs having the abovementioned advantages, in combination with a pharmaceutically acceptable vehicle.

Another purpose of the present invention is to provide cartridges for external decontamination, inside which novel PTEs are grafted, in particular for decontaminating the blood of an individual poisoned with organophosphorus compounds.

Another purpose of the present invention is to provide the bacteria transformed using nucleotide sequences encoding for these novel PTEs and expressing the latter in their cytoplasm or at their surface, said bacteria transformed in this way being capable of being used in their turn within the context of organophosphorus compound decontamination.

DETAILED DESCRIPTION OF THE INVENTION

A subject of the invention is mutated hyperthermophilic phosphotriesterases (PTEs) possessing a lactonase activity derived from the hyperthermophilic PTEs corresponding to the consensus sequence SEQ ID NO: 1, and comprising at least one of the following four mutations:
substitution of the tyrosine Y in position 98,
substitution of the tyrosine Y in position 100,
substitution of the arginine R in position 224,
substitution of the cysteine C in position 259,
of SEQ ID NO: 1 by any other natural or non-natural amino acid, said mutated hyperthermophilic phosphotriesterases (PTEs) possessing a lactonase activity greater than that of the non-mutated hyperthermophilic phosphotriesterases (PTEs) from which they are derived.

The abovementioned mutated hyperthermophilic PTEs of the invention possessing a lactonase activity have the advantage of being thermostable, namely of being proteins capable of retaining their enzymatic activity at temperatures up to 95° C. (Merone et al., 2005). The enzymatic activity of the abovementioned mutated hyperthermophilic PTEs of the invention corresponds in particular to the hydrolysis activity of OPs as measured according to the method described previously (Merone et al., 2005). This thermostability confers upon them the advantage of being inexpensive to produce, on the one hand because they are stable in organic solvents which makes them more suitable for industrial processes, and, on the other hand, because they are very inexpensive to purify by the technique of heating the cell lysates of the cells producing these PTEs, such as *E. coli*; a large yield and high purity are thus obtained in one stage.

The abovementioned mutated hyperthermophilic PTEs of the invention possessing a lactonase activity also have the advantage of being more active within the context of the hydrolysis of the OPs (in particular according to the abovementioned method) than the wild-type hyperthermophilic PTEs from which they are derived. The abovementioned mutated hyperthermophilic PTEs possessing a lactonase activity also have the advantage of being more active within the context of "quorum quenching" than the wild-type hyperthermophilic PTEs from which they are derived, i.e. within the context of resistance to pathogen infections.

A more particular subject of the invention is the abovementioned mutated hyperthermophilic phosphotriesterases, derived from the hyperthermophilic PTE of *Sulfolobus solfataricus* corresponding to the sequence SEQ ID NO: 3, or of the hyperthermophilic PTE of *Sulfolobus acidocaldarius* corresponding to the sequence SEQ ID NO: 5, said sequences SEQ ID NO: 3 and SEQ ID NO: 5 belonging to the consensus sequence SEQ ID NO: 1, the amino acid in position 2 in SEQ ID NO: 1 being missing from SEQ ID NO: 3.

The invention relates more particularly to the abovementioned mutated hyperthermophilic phosphotriesterases possessing a lactonase activity, comprising at least the following four mutations:
substitution of the tyrosine Y in position 98,
substitution of the tyrosine Y in position 100,
substitution of the arginine R in position 224,
substitution of the cysteine C in position 259,
of SEQ ID NO: 1 by any other natural or non-natural amino acid.

A more particular subject of the invention is the abovementioned mutated hyperthermophilic phosphotriesterases possessing a lactonase activity, characterized in that they also comprise at least one of the following mutations:
substitution of the valine V in position 28,
substitution of the proline P in position 68,
substitution of the threonine T in position 69,
substitution of the leucine L in position 73,
substitution of the aspartate D in position 142,
substitution of the glycine G in position 226,
substitution of the leucine L in position 227,
substitution of the phenylalanine F in position 230,
substitution of the tryptophan W in position 264,
substitution of the tryptophan W in position 279,
of SEQ ID NO: 1 by any other natural or non-natural amino acid.

The invention relates more particularly to the abovementioned mutated hyperthermophilic phosphotriesterases possessing a lactonase activity, characterized in that they comprise the following five mutations:
  substitution of the valine V in position 28,
  substitution of the leucine L in position 73,
  substitution of the aspartate D in position 142,
  substitution of the glycine G in position 226,
  substitution of the leucine L in position 227,
of SEQ ID NO: 1 by any other natural or non-natural amino acid.

A more particular subject of the invention is the abovementioned mutated hyperthermophilic phosphotriesterases possessing a lactonase activity, characterized in that they comprise the following five mutations:
  substitution of the proline P in position 68,
  substitution of the threonine T in position 69,
  substitution of the phenylalanine F in position 230,
  substitution of the tryptophan W in position 264,
  substitution of the tryptophan W in position 279,
of SEQ ID NO: 1 by any other natural or non-natural amino acid.

The invention relates more particularly to the abovementioned mutated hyperthermophilic phosphotriesterases possessing a lactonase activity, derived from the hyperthermophilic PTEs corresponding to the consensus sequence SEQ ID NO: 1, characterized in that they comprise at least one of the following four mutations:
  substitution of the tyrosine Y in position 98 by a tryptophan W,
  substitution of the tyrosine Y in position 100 by a phenylalanine F,
  substitution of the arginine R in position 224 by a histidine H,
  substitution of the cysteine C in position 259 by a leucine L,
and, if appropriate, at least one of the following mutations:
  substitution of the valine V in position 28 by an alanine A,
  substitution of the proline P in position 68 by a valine V,
  substitution of the threonine T in position 69 by a serine S,
  substitution of the leucine L in position 73 by an isoleucine I,
  substitution of the aspartate D in position 142 by a threonine T,
  substitution of the glycine G in position 226 by a proline P,
  substitution of the leucine L in position 227 by a histidine H,
  substitution of the phenylalanine F in position 230 by a serine S,
  substitution of the tryptophan W in position 264 by an alanine A,
  substitution of the tryptophan W in position 279 by an isoleucine I.

A more particular subject of the invention is the abovementioned mutated hyperthermophilic phosphotriesterases possessing a lactonase activity, derived from the hyperthermophilic PTE of *Sulfolobus solfataricus* corresponding to the sequence SEQ ID NO: 3, and comprising at least one of the following four mutations:
  substitution of the tyrosine Y in position 97,
  substitution of the tyrosine Y in position 99,
  substitution of the arginine R in position 223,
  substitution of the cysteine C in position 258,
of SEQ ID NO: 3 by any other natural or non-natural amino acid.

The invention relates more particularly to the abovementioned mutated hyperthermophilic phosphotriesterases possessing a lactonase activity, derived from the hyperthermophilic PTE of *Sulfolobus solfataricus* corresponding to the sequence SEQ ID NO: 3, and comprising at least the following four mutations:
  substitution of the tyrosine Y in position 97,
  substitution of the tyrosine Y in position 99,
  substitution of the arginine R in position 223,
  substitution of the cysteine C in position 258,
of SEQ ID NO: 3 by any other natural or non-natural amino acid.

A more particular subject of the invention is the abovementioned mutated hyperthermophilic phosphotriesterases possessing a lactonase activity, derived from the hyperthermophilic PTE of *Sulfolobus solfataricus* corresponding to the sequence SEQ ID NO: 3, characterized in that they also comprise at least one of the following mutations:
  substitution of the valine V in position 27,
  substitution of the proline P in position 67,
  substitution of the threonine T in position 68,
  substitution of the leucine L in position 72,
  substitution of the aspartate D in position 141,
  substitution of the glycine G in position 225,
  substitution of the leucine L in position 226,
  substitution of the phenylalanine F in position 229,
  substitution of the tryptophan W in position 263,
  substitution of the tryptophan W in position 278,
of SEQ ID NO: 3 by any other natural or non-natural amino acid.

The invention relates more particularly to the abovementioned mutated hyperthermophilic phosphotriesterases possessing a lactonase activity, derived from the hyperthermophilic PTE of *Sulfolobus solfataricus* corresponding to the sequence SEQ ID NO: 3, characterized in that they comprise the following five mutations:
  substitution of the valine V in position 27,
  substitution of the leucine L in position 72,
  substitution of the aspartate D in position 141,
  substitution of the glycine G in position 225,
  substitution of the leucine L in position 226,
of SEQ ID NO: 3 by any other natural or non-natural amino acid.

A more particular subject of the invention is the abovementioned mutated hyperthermophilic phosphotriesterases possessing a lactonase activity, derived from the hyperthermophilic PTE of *Sulfolobus solfataricus* corresponding to the sequence SEQ ID NO: 3, characterized in that they comprise the following five mutations:
  substitution of the proline P in position 67,
  substitution of the threonine T in position 68,
  substitution of the phenylalanine F in position 229,
  substitution of the tryptophan W in position 263,
  substitution of the tryptophan W in position 278,
of SEQ ID NO: 3 by any other natural or non-natural amino acid.

The invention relates more particularly to the abovementioned mutated hyperthermophilic phosphotriesterases possessing a lactonase activity, derived from the hyperthermophilic PTE of *Sulfolobus solfataricus* corresponding to the sequence SEQ ID NO: 3, characterized in that they comprise at least one of the following four mutations:
  substitution of the tyrosine Y in position 97 by a tryptophan W,
  substitution of the tyrosine Y in position 99 by a phenylalanine F,
  substitution of the arginine R in position 223 by a histidine H,
  substitution of the cysteine C in position 258 by a leucine L,
and, if appropriate, at least one of the following mutations:

substitution of the valine V in position 27 by an alanine A,
substitution of the proline P in position 67 by a valine V,
substitution of the threonine T in position 68 by a serine S,
substitution of the leucine L in position 72 by an isoleucine I,
substitution of the aspartate D in position 141 by a threonine T,
substitution of the glycine G in position 225 by a proline P,
substitution of the leucine L in position 226 by a histidine H,
substitution of the phenylalanine F in position 229 by a serine S,
substitution of the tryptophan W in position 263 by an alanine A,
substitution of the tryptophan W in position 278 by an isoleucine I.

A more particular subject of the invention is the abovementioned mutated hyperthermophilic phosphotriesterases possessing a lactonase activity, derived from the hyperthermophilic PTE of *Sulfolobus solfataricus* corresponding to the sequence SEQ ID NO: 3, characterized in that they correspond to the following sequences:

SEQ ID NO: 7 corresponding to the sequence SEQ ID NO: 3 comprising the following four mutations:
substitution of the tyrosine Y in position 97 by a tryptophan W,
substitution of the tyrosine Y in position 99 by a phenylalanine F,
substitution of the arginine R in position 223 by a histidine H,
substitution of the cysteine C in position 258 by a leucine L, SEQ ID NO: 9 corresponding to the sequence SEQ ID NO: 7 additionally comprising the following five mutations:
substitution of the valine V in position 27 by an alanine A,
substitution of the leucine L in position 72 by an isoleucine I,
substitution of the aspartate D in position 141 by a threonine T,
substitution of the glycine G in position 225 by a proline P,
substitution of the leucine L in position 226 by a histidine H, SEQ ID NO: 11 corresponding to the sequence SEQ ID NO: 9 additionally comprising the following five mutations:
substitution of the proline P in position 67 by a valine V,
substitution of the threonine T in position 68 by a serine S,
substitution of the phenylalanine F in position 229 by a serine S,
substitution of the tryptophan W in position 263 by an alanine A,
substitution of the tryptophan W in position 278 by an isoleucine I.

The invention relates more particularly to the abovementioned mutated hyperthermophilic phosphotriesterases possessing a lactonase activity, derived from the hyperthermophilic PTE of *Sulfolobus solfataricus* corresponding to the sequence SEQ ID NO: 3, characterized in that they comprise at least one mutation corresponding to the substitution of at least one of the amino acids in the following amino acid pairs the positions of which in SEQ ID NO: 3 are indicated hereafter, by another natural or non-natural amino acid: 2R/314S, 14K/12E, 26R/75D, 26R/42E, 33R/42E, 33R/45E, 55R/52E, 55R/285E, 74R/121D, 81K/42E, 81K/43D, 84K/80E, 109R/113E, 123K/162E, 147K/148D, 151K/148D, 154R/150E, 154R/187E, 154R/188E, 161K/188E, 183R/150E, 183R/187E, 183R/180E, 210K/245D, 215K/214D, 223R/256D, 223R/202D, 234K/204D, 235R/202D, 241R/245D, 245D/244K, 250K/249D, 277R/286D, 292K/298E, 310K/307E.

A more particular subject of the invention is the abovementioned mutated hyperthermophilic phosphotriesterases possessing a lactonase activity, derived from the hyperthermophilic PTE of *Sulfolobus acidocaldarius* corresponding to the sequence SEQ ID NO: 5, and comprising at least one of the following four mutations:
substitution of the tyrosine Y in position 98,
substitution of the tyrosine Y in position 100,
substitution of the arginine R in position 224,
substitution of the cysteine C in position 259,
of SEQ ID NO: 5 by any other natural or non-natural amino acid.

The invention relates more particularly to the abovementioned mutated hyperthermophilic phosphotriesterases possessing a lactonase activity, derived from the hyperthermophilic PTE of *Sulfolobus acidocaldarius* corresponding to the sequence SEQ ID NO: 5, comprising at least the following four mutations:
substitution of the tyrosine Y in position 98,
substitution of the tyrosine Y in position 100,
substitution of the arginine R in position 224,
substitution of the cysteine C in position 259,
of SEQ ID NO: 5 by any other natural or non-natural amino acid.

A more particular subject of the invention is the abovementioned mutated hyperthermophilic phosphotriesterases possessing a lactonase activity, derived from the hyperthermophilic PTE of *Sulfolobus acidocaldarius* corresponding to the sequence SEQ ID NO: 5, characterized in that they also comprise at least one of the following mutations:
substitution of the valine V in position 28,
substitution of the proline P in position 68,
substitution of the threonine T in position 69,
substitution of the leucine L in position 73,
substitution of the aspartate D in position 142,
substitution of the glycine G in position 226,
substitution of the leucine L in position 227,
substitution of the phenylalanine F in position 230,
substitution of the tryptophan W in position 264,
substitution of the tryptophan W in position 279,
of SEQ ID NO: 5 by any other natural or non-natural amino acid.

The invention relates more particularly to the abovementioned mutated hyperthermophilic phosphotriesterases possessing a lactonase activity, derived from the hyperthermophilic PTE of *Sulfolobus acidocaldarius* corresponding to the sequence SEQ ID NO: 5, characterized in that they comprise the following five mutations:
substitution of the valine V in position 28,
substitution of the leucine L in position 73,
substitution of the aspartate D in position 142,
substitution of the glycine G in position 226,
substitution of the leucine L in position 227,
of SEQ ID NO: 5 by any other natural or non-natural amino acid.

A more particular subject of the invention is the abovementioned mutated hyperthermophilic phosphotriesterases possessing a lactonase activity, derived from the hyperthermophilic PTE of *Sulfolobus acidocaldarius* corresponding to the sequence SEQ ID NO: 5, characterized in that they comprise the following five mutations:

substitution of the proline P in position 68,
substitution of the threonine T in position 69,
substitution of the phenylalanine F in position 230,
substitution of the tryptophan W in position 264,
substitution of the tryptophan W in position 279,
of SEQ ID NO: 5 by any other natural or non-natural amino acid.

The invention relates more particularly to the abovementioned mutated hyperthermophilic phosphotriesterases possessing a lactonase activity, derived from the hyperthermophilic PTE of *Sulfolobus acidocaldarius* corresponding to the sequence SEQ ID NO: 5, characterized in that they comprise at least one of the following four mutations:
substitution of the tyrosine Y in position 98 by a tryptophan W,
substitution of the tyrosine Y in position 100 by a phenylalanine F,
substitution of the arginine R in position 224 by a histidine H,
substitution of the cysteine C in position 259 by a leucine L,
and, if appropriate, at least one of the following mutations:
substitution of the valine V in position 28 by an alanine A,
substitution of the proline P in position 68 by a valine V,
substitution of the threonine T in position 69 by a serine S,
substitution of the leucine L in position 73 by an isoleucine I,
substitution of the aspartate D in position 142 by a threonine T,
substitution of the glycine G in position 226 by a proline P,
substitution of the leucine L in position 227 by a histidine H,
substitution of the phenylalanine F in position 230 by a serine S,
substitution of the tryptophan W in position 264 by an alanine A,
substitution of the tryptophan W in position 279 by an isoleucine I.

A more particular subject of the invention is the abovementioned mutated hyperthermophilic phosphotriesterases possessing a lactonase activity, derived from the hyperthermophilic PTE of *Sulfolobus acidocaldarius* corresponding to the sequence SEQ ID NO: 5, characterized in that they correspond to the following sequences:
SEQ ID NO: 13 corresponding to the sequence SEQ ID NO: 5 comprising the following four mutations:
substitution of the tyrosine Y in position 98 by a tryptophan W,
substitution of the tyrosine Y in position 100 by a phenylalanine F,
substitution of the arginine R in position 224 by a histidine H,
substitution of the cysteine C in position 259 by a leucine L,
SEQ ID NO: 15 corresponding to the sequence SEQ ID NO: 13 additionally comprising the following five mutations:
substitution of the valine V in position 28 by an alanine A,
substitution of the leucine L in position 73 by an isoleucine I,
substitution of the aspartate D in position 142 by a threonine T,
substitution of the glycine G in position 226 by a proline P,
substitution of the leucine L in position 227 by a histidine H,
SEQ ID NO: 17 corresponding to the sequence SEQ ID NO: 15 additionally comprising the following five mutations:
substitution of the proline P in position 68 by a valine V,
substitution of the threonine T in position 69 by a serine S,
substitution of the phenylalanine F in position 230 by a serine S,
substitution of the tryptophan W in position 264 by an alanine A,
substitution of the tryptophan W in position 279 by an isoleucine I.

A more particular subject of the invention is the abovementioned mutated hyperthermophilic phosphotriesterases possessing a lactonase activity, in which at least one of the amino acids involved in the salt bridges is modified by substitution or deletion, such that the activation temperature of said mutated hyperthermophilic phosphotriesterases possessing a lactonase activity is reduced compared with the activation temperature of the mutated hyperthermophilic phosphotriesterases possessing a lactonase activity in which the amino acids involved in the salt bridges is unmodified.

In an advantageous embodiment of the invention, the amino acids involved in the salt bridges mentioned previously can be replaced by a sequence of at least two amino acids. This is then an addition.

It is understood in the invention that the term "substitution" corresponds to the replacement of one amino acid by another. The substitutions can be conservative, i.e. the substituted amino acid is replaced by an amino acid of the same structure or with the same physico-chemical property (polar, hydrophobic, acid, basic amino acids etc.) such that the three-dimensional structure of the protein remains unchanged, or by contrast non-conservative. The substitutions defined according to the invention relate equally to natural amino acids, or artificial amino acids. Thus, the amino acids involved in the salt bridges can be replaced by a natural amino acid or an artificial amino acid.

It is also understood in the invention that the "deletion" corresponds to the removal of an amino acid, such that the protein sequence which has been subjected to said deletion is shorter than the sequence which has not been subjected to said deletion.

Study of the three-dimensional structure of the hyperthermophilic PTEs has made it possible to detect the amino acids involved in the salt bridges. These significant amino acids are charged and have an interaction distance of less than 5.5 Å. If the protein, although possessing mutations in the active site, mentioned previously, does not possess sufficient activity compared to the mesophilic PTEs, it is possible to mutate the amino acids involved in the salt bridges. These mutations have the effect of interfering with the interactions, and making the protein more flexible.

The crystallographic data have made it possible to show 25 interactions with a distance of less than 4 Å, 6 interactions with distances comprised between 4 Å and 5 Å, and 4 interactions with distances comprised between 5 Å and 5.5 Å. The abovementioned interactions involve 2 amino acids. Thus, in total, 52 amino acids are involved in the salt bridges.

The amino acids involved in these interactions, as well as the distance of the interaction of said amino acids are indicated in Table 1 below.

TABLE 1 interactions involved in the salt bridges of the protein SsoPox

| D < 4 Å | 4 Å < D < 5 Å | 5 Å < D < 5.5 Å |
|---|---|---|
| 2R ↔ 314S-COOH | 33R ↔ 42E | 145R ↔ 187E |
| 14K ↔ 12E | 81K ↔ 42E | 183R ↔ 150E |
| 26R ↔ 75D | 84K ↔ 80E | 215R ↔ 214D |
| 26R ↔ 42E | 147K ↔ 148D | 244K ↔ 245D |
| 33R ↔ 45E | 161K ↔ 188E | |
| 55R ↔ 52E | 310K ↔ 307E | |
| 55R ↔ 285E | | |
| 74R ↔ 121D | | |
| 81K ↔ 43D | | |
| 109R ↔ 113E | | |
| 123K ↔ 162E | | |
| 151K ↔ 148D | | |
| 154R ↔ 150E | | |
| 154R ↔ 188E | | |
| 183R ↔ 187E | | |
| 183R ↔ 180E | | |
| 210K ↔ 245D | | |
| 223R ↔ 256D | | |
| 223R ↔ 202D | | |
| 234K ↔ 204D | | |
| 235R ↔ 202D | | |
| 241R ↔ 245D | | |
| 250K ↔ 249D | | |
| 277R ↔ 286D | | |
| 292K ↔ 298E | | |

In an advantageous embodiment of the invention, in the abovementioned mutated hyperthermophilic phosphotriesterases possessing a lactonase activity of Sso, at least one of the amino acids in the following positions 2, 12, 14, 26, 33, 42, 43, 45, 52, 55, 74, 75, 80, 81, 84, 109, 113, 121, 123, 145, 147, 148, 150, 151, 154, 161, 162, 180, 183, 187, 188, 202, 204, 210, 214, 215, 223, 234, 235, 241, 244, 245, 249, 250, 256, 277, 285, 286, 292, 298, 307 and 310 is modified. The position of the previous amino acids is defined with respect to the first amino acid of the protein SsoPox.

In an advantageous embodiment of the invention, in the abovementioned mutated hyperthermophilic phosphotriesterases possessing a lactonase activity of Sac, at least one of the amino acids in the following positions 3, 13, 15, 27, 34, 43, 44, 46, 53, 56, 75, 76, 81, 82, 85, 110, 114, 122, 124, 146, 148, 149, 151, 152, 155, 162, 163, 181, 184, 188, 189, 203, 205, 211, 215, 216, 224, 235, 236, 242, 245, 246, 250, 251, 257, 278, 286, 287, 293, 299, 308 and 311 is modified. The position of the previous amino acids is defined with respect to the first amino acid of the protein SacPox.

The invention also relates to the nucleotide sequences encoding the mutated hyperthermophilic phosphotriesterases possessing a lactonase activity as defined above.

A subject of the invention is also the vectors, in particular plasmids, containing nucleotide sequences encoding the mutated hyperthermophilic phosphotriesterases possessing a lactonase activity as defined above.

The invention also relates to the host cells, in particular the bacteria, transformed using a vector as defined above, such that their genome contains nucleotide sequences encoding the mutated hyperthermophilic phosphotriesterases possessing a lactonase activity as defined above, said mutated hyperthermophilic PTEs possessing a lactonase activity being produced in the cytoplasm of the host cells, or secreted at their surface.

The invention also relates to the host cells, in particular bacteria, coupled with the mutated hyperthermophilic phosphotriesterases possessing a lactonase activity as defined above, or having mutated hyperthermophilic phosphotriesterases possessing a lactonase activity as defined above, grafted onto their surface.

The invention also relates to transgenic organisms, in particular mammals, transformed using a vector as defined above, said transgenic organisms being resistant to pathogens.

A subject of the invention is also the use of mutated hyperthermophilic phosphotriesterases possessing a lactonase activity as defined above, or of the abovementioned transformed host cells, as bioscavengers within the context of the decontamination of the surfaces of materials, of the skin or mucous membranes, contaminated with organophosphorus compounds, or with bacteria or within the context of the preparation of medicaments (or bio-medicaments) which can be used within the context of the prevention or treatment of an external contamination or of an internal poisoning by ingestion or inhalation of organophosphorus compounds, or within the context of the preparation of medicaments which can be used within the context of the prevention or treatment of a bacterial infection, or within the context of the pollution control of water polluted with organophosphorus compounds, or within the context of the destruction of stocks of neurotoxic agents.

A subject of the invention is also materials impregnated with mutated hyperthermophilic phosphotriesterases possessing a lactonase activity as defined above, in liquid or solid form, such as gloves, various garments (in particular fixing to fabrics for chemical protection suits), wipes, spray foams.

The invention also relates to kits for the decontamination of the surfaces of materials, of the skin or mucous membranes, contaminated with organophosphorus compounds, or for the pollution control of water polluted with organophosphorus compounds, characterized in that they comprise mutated hyperthermophilic phosphotriesterases possessing a lactonase activity as defined above (if appropriate in lyophilized form), or materials impregnated with the abovementioned mutated hyperthermophilic phosphotriesterases possessing a lactonase activity.

A subject of the invention is also scavengers for the abovementioned organophosphorus compounds, having the advantage of being extremely sensitive thanks to the capabilities described above of the mutated hyperthermophilic phosphotriesterases possessing a lactonase activity as defined above.

The invention also relates to cartridges for external decontamination, inside which mutated hyperthermophilic phosphotriesterases possessing a lactonase activity as defined above according to the invention are grafted, which can be used in particular for decontaminating the blood of an individual poisoned with organophosphorus compounds.

The invention also relates to pharmaceutical compositions characterized in that they comprise mutated hyperthermophilic phosphotriesterases possessing a lactonase activity as defined above, in combination with a pharmaceutically acceptable vehicle.

A subject of the invention is also pharmaceutical compositions as defined above, characterized in that they are presented in a form which can be administered by injectable route in particular in solution or packaged or pegylated, or by topical route, in particular in the PEGylated or encapsulated form or in the form of ointment, aerosol or wipes.

The invention also relates to the use of abovementioned impregnated materials, or of cartridges for external decontaminations defined above, as antiseptics for the decontamination of surface bacterial infection.

The invention also relates to the use of the pharmaceutical composition defined previously, for the treatment of bacterial infections, in particular in the blood.

The invention is further illustrated by the following detailed description of the phosphotriesterase of *Sulfolobus*

*solfataricus*, and mutations made to the latter within the context of the preparation of mutated hyperthermophilic phosphotriesterases possessing a lactonase activity as defined above according to the invention.

The organophosphorus compounds (OPs) are highly toxic molecules which make up certain chemical warfare agents and pesticides. These products at present represent a serious public health problem (poisonings, soil pollution, water pollution). Unfortunately, the solutions currently available are unsatisfactory. Nevertheless, biotechnologies constitute an extremely promising alternative. In fact, certain enzymes which can be used as "bioscavengers" are capable of very effectively destroying a broad spectrum of these poisons.

I) Structural Study of the Phosphotriesterase of *Sulfolobus solfataricus*

This enzyme, originating from an archaeon, possesses the characteristic of being hyperthermophilic. Its study makes it possible to deepen knowledge of the thermostable proteins. This protein, capable of hydrolyzing the OPs, is a potential candidate for environmental and cutaneous decontaminations. This work therefore serves as a basis for obtaining active and thermostable enzymes by bio-engineering. This last characteristic allows large-scale production at low cost. The recombinant protein, produced by a mesophilic organism such as *Escherichia coli*, can be effectively purified in one stage. The cell lysates are heated, leading to the precipitation of the mesophilic proteins of the host. Only the hyperthermostable protein remains soluble.

Works have also made it possible to demonstrate that SsoPox is a natural lactonase with a promiscuous phosphotriesterase activity (Elias et al., 2007b).

Thanks to its "quorum quenching" activity, its ease of production at low cost, and its great stability which makes it compatible with the constraints of industrial processes, SsoPox is a promising candidate for combating bacterial infections using the quorum quenching route.

A) Material and Methods

1. Crystallization

The cloning, the expression, and the purification of the hyperthermophilic PTE of *S. Solfataricus* in *E. coli* are described by Merone et al. (2005). The enzyme was concentrated to 5.8 mg·mL$^{-1}$. The crystallization tests were carried out using the hanging-drop vapour diffusion method. Equal volumes, ranging from 1 to 2 µL of protein solution and of the reservoir solution were mixed. The resulting drops were placed in equilibrium with a reservoir solution containing 15 to 18% (mass/volume) of polyethylene glycol (PEG) 8000 in Tris-HCl buffer, pH 8. Very fine crystals appear after a week at 4° C.

2. Data Collection

The crystals were first transferred to a cryoprotective solution made up of the reservoir solution and 25% (volume/volume) glycerol. Each crystal was then instantly frozen in liquid nitrogen. The X-ray diffraction data were collected at 100° K. on the beamline FIP BM 30 of the Grenoble synchrotron. (ESRF, Grenoble, France). For these collections, a Mar CCD detector (165 mm) was used. A set of data was recorded at a resolution of 2.6 Å.

3. Determination of the Structure

The diffraction data were integrated and adjusted to scale by means of the XDS2000 programs and the CCP4 (Collaborative Computational Project) software suite. The first molecule replacement was carried out with PHASER using a polyalanine model deduced from the structure of the PTE of *P. diminuta* (PDB code: 1DPM). Two protein molecules were found in the asymmetrical unit. The active site constituted by two metal ions was clearly visible. The electron density map was improved using a process of solvent flattening and the non-crystallographic symmetry averaging of the two molecules by means of the DM software. The manual construction of the model was carried out using the COOT program. It was possible to place certain side chains and a few loops involved in the dimer interface have had to be removed. A new molecular replacement was carried out using MOLREP, by fixing the first two solutions found and using the thus-improved model. Two additional solutions were found, producing a total of four molecules in the asymmetrical unit (R=46%, Rfree=51%). The structure model was then constructed manually and refined by sequences of the COOT and REFMAC software cycles.

B) Results

1. Three-Dimensional Structure

The PTE of *S. solfataricus* crystallizes in PEG and the diffraction data were collected with the synchrotron (ESRF, Grenoble, France). The structure of this protein was determined by the molecule replacement method (see Material and Methods), and refined at a resolution of 2.6 Å with an R factor of 21.8%, an Rfree factor of 28% and good geometry. The main chain is completely visible in the density map, for the two homodimers of the asymmetrical unit, despite an average resolution.

The structure of this hyperthermophilic PTE is such that the molecule is approximately globular with dimensions of approximately 40 Å×54 Å×46 Å. Its topology is very similar to the two mesophilic PTEs the structures of which are already known. The first originates from *P. diminuta* (Vanhooke et al., 1994; pdb code: 1DPM) and the second originates from *A. radiobacter* (Jackson et al., 2005; code pdb: 2D2J). This hyperthermostable structure can be described as a distorted $(\beta/\alpha)_8$ barrel also called a TIM barrel. It consists of 8 parallel β strands forming the barrel flanked by 11 α helices. The superposition of these three resolved structures produces average deviations (RMS) for the position of the α carbons between the PTE of *S. solfataricus* and that of *P. diminuta* (over 268 atoms) and between the PTE of *S. solfataricus* and that of *A. radiobacter* (over 271 atoms) of 1.05 Å and 1.11 Å, respectively.

There are a few major differences, namely two shortenings of the structure of the PTE of *S. solfataricus* compared with the structures of the mesophilic PTEs. The first is located at the entrance to the active site and consists of the deletion of a loop of 15 residues. The other shortening concerns the two ends of the polypeptide chain. In fact, there are 6 and 2 residues less at the C-terminal end, and 2 and 4 residues less at the N-terminal end, compared with the PTEs of *P. diminuta* and of *A. radiobacter*, respectively. Another modification relates to the presence, in the structure of the PTE of *S. solfataricus*, of additional loops involved in the dimerization.

2. Dimer Interface

Just like the mesophilic PTEs (Benning et al., 1994; Jackson et al., 2005), the PTE of *S. solfataricus* crystallizes as a homodimer. For the two mesophilic PTEs, the area of contact between the monomers is approximately 1350 Å$^2$, with 62.5% hydrophobic contacts, and there are approximately 25 hydrogen bonds at the interface. In the structure of the PTE of *S. solfataricus*, the additional loops involved in the formation of the dimer increase the contact surface. The two monomers thus seem to interpenetrate each other. In fact, the area of contact is 1720 Å$^2$. Despite this increase, the quantity of hydrogen bonds at the interface is of the same order (approximately 20). In fact, this increase in the contact surface is essentially due to additional hydrophobic contacts. Thus, the hydrophobic contacts at the interface represent 68% of all the contacts in this dimer.

Moreover, the conformation of the dimer is not identical to that of the mesophilic PTEs. There is a clear movement of the relative position of the second monomer which could have been caused by the additional loops involved in the dimerization.

Another interesting point relates to the overall accessibility to the solvent of protein. In fact, all these PTEs: that of *P. diminuta*, *A. radiobacter* and *S. solfataricus*, have approximately the same accessibility to the solvent with respect to the monomers (13076.1 $Å^2$, 12828.7 $Å^2$, 13039.4 $Å^2$, respectively), and approximately the same volume (42464.2 $Å^3$, 44313.2 $Å^3$, 43429.9 $Å^3$ respectively). By contrast, the hyperthermostable dimer is smaller (86950 $Å^3$) than the mesophilic dimers (88800 $Å^3$).

3. Electrostatic Potential

The electrostatic potential analyses with a Swiss-Pdb-Viewer reveal that the PTE of *S. solfataricus* is a highly charged protein. In fact, the structure shows 39 Asp and Glu, 37 Lys and Arg representing a lot of charges located on the surface of the protein. This very high number of charged residues is the cause of the presence of numerous clusters of charges. One face is mainly negatively charged, the other rather positively. This particular charge distribution must confer a very strong dipole moment on the protein. Moreover, the boundaries between the two monomers are uniformly negatively charged. This is very surprising, because non-complementary charges would rather tend to increase the repulsion energy between the two monomers. A single region of the protein has a low charge. This is a hydrophobic pocket, which corresponds to the active site. The latter is surrounded by negative charges.

4. Ionic Bonds

In order to compensate for the coupling energies induced by this large number of charges and the strong dipole moment, half of these charged surface residues are involved in salt bridges. The PTE of *S. solfataricus* has 25 salt bridges per monomer compared with the 15 units in the case of the mesophilic PTEs. The majority of these salt bridges are uniformly located at the surface of the protein. As described for other hyperthermophilic proteins, this large number of salt bridges form complex networks of charges at the surface of the protein.

5. Description of the Active Site

Like the mesophilic PTEs, the active site of the PTE of *S. solfataricus* consists of a bimetallic centre, located at the C-terminal end of the β barrel. These two metallic cations are bridged by the catalytic water molecule, and by a modified residue, a carboxylated lysine. The enzyme uses a carboxylated lysine rather than a glutamate probably because the pair of electrons borne by the nitrogen can be delocalized, and thus allow each of the oxygens to bear a negative charge, and thus compensate for the four formal positive charges of the two metals. For their coordination, four histidines are also involved, as well as an aspartic acid (Asp 256) and another water molecule. The most concealed metal (called a) adopts a trigonal bipyramid geometry, coordinated by His 22, His 24, Asp 256, Lys 137 and the bridging water molecule. The metal most exposed to the solvent (called β) adopts a distorted trigonal bipyramid geometry with His 170, His 199, Lys 137, the bridging water molecule and another water molecule as ligands. The bridging water molecule is equidistant from the two metals, with a distance of approximately 2 Å, and is in a hydrogen bond with Asp 256 (2.68 Å). In the PTE of *S. solfataricus*, the metallic centre, the four histidines, the aspartate and the carboxylated lysine are preserved and overlap well with the other known structures of PTEs. The structural comparison with the two mesophilic PTEs has led to the identification of the binding site of the phosphotriesters according to the site described (Chen-Goodspeed et al., 2001). The chemical nature of the side chains in the cavity is unchanged overall compared with the mesophilic PTEs, which probably leads to a similar binding of the phosphotriesters in the active site of the PTE of *S. solfataricus*.

Although the folding is similar overall to the mesophilic PTEs, the active site of the PTE of *S. solfataricus* is much narrower, due to a slight modification of the peptide skeleton and the presence of two tyrosines (Tyr 97 and Tyr 99). Moreover, at the entrance to the active site, a loop of nine residues creates a hydrophobic tunnel, which is connected to the active site. This has not been described in the structures of the mesophilic PTEs.

C) Conclusion

1. Thermostability

The PTE of *S. solfataricus* is an extremely stable enzyme. In fact, it is active vis-à-vis paraoxon up to very high temperatures. Merone et al. (2005), have not, moreover, found its maximum activity for technical reasons, but up to 95° C., the activity continues to increase. The structural study of this protein shows a few indices making it possible to explain the mechanism of this extraordinary thermostability.

1.1 The Shortening of the Structure

The structure of the *S. solfataricus* PTE shows the deletion of a large loop compared with the mesophilic PTEs (see results). This is a standard case, because the loops of the thermostable proteins are very often shorter than those of their mesophilic homologues (Vieille C., 1996), which makes it possible to stabilize the native configuration, or to discriminate against the denatured state. In this thermostable structure, the two ends of the chain are shortened and more anchored to the core of the protein. Furthermore, in order to reinforce this compact core, these two ends are in ionic interaction between the terminal carboxylic acid (Ser 314) and the side chain of Arg 2. It can also be noted that two proline residues (Pro 4 and Pro 309) stiffen these ends a little more. This type of mutual stabilization between the N-terminal and the C-terminal ends is considered to be a factor increasing the overall rigidity of the proteins, and has also been described in the phosphoribosyl anthranilate isomerase of *T. maritima*. In fact, the reduction in the flexibility of the loops and of the ends of the peptide skeleton by their stabilization via a salt bridge, or their shortening or their deletion, contributes to the overall increase in the stability of the protein.

1.2 Dimer Association

The additional loops involved in the thermostable dimer have consequences. The first concerns the assembly of the monomers. In fact, the conformation of this dimer is different from the conformation of the standard TIM dimer. A similar fact has already been described for the TIM dimer of Ttx (Walden et al. 2004).

Another direct consequence involves the increase in the contact surface between the two monomers, and leads to an extreme value for the permanent complexes (Lo Conte L. et al., 1999) (see results). The reinforcement of this interaction confirms that the dimerization is an important means of thermostabilization (Vieille et al., 2001). The extreme hydrophobicity of this contact surface (Lo Conte L. et al., 1999) must be an important factor in stabilization, given that the hydrophobic contacts are more favourable at high temperature.

These additional loops involved in the dimer also induce a modification of the volume of the dimer. In fact, the monomers of this hyperthermostable protein have approximately the same volume as the monomers of the mesophilic PTEs. On the other hand, its dimer is much smaller. This is consistent with the fact that the minimization of the surface/volume ratio, as is the case for this protein, can simultaneously increase the stability of the proteins by reducing the energy induced by the unfavourable surfaces, while increasing the internal attraction interactions (Sterner and Liebl, 2001).

The observed reinforcement of this dimer is consistent with the preference of the hyperthermostable proteins to organize themselves into oligomers. This has also been described for TIM proteins (Walden et al., 2004).

1.3 Comparison of the Sequences

The sequence of this hyperthermostable protein shows an amino acid composition which is different to those of the mesophilic PTEs (Merone et al., 2005). In fact, in this *S. solfataricus* protein there is a decrease in the content of uncharged polar amino acids such as Gln, Asn, Thr and Ser. In fact, 50 (15.9% of the total residues) of them are present in the thermostable PTE, while there are 65 and 60 (18.3% and 19.7% of the total residues) of them in the sequences of the PTEs of *P. diminuta* and of *A. radiobacter* respectively. This difference is a typical value between hyperthermophilic and mesophilic proteins (Sterner and Liebl, 2001). The residues Gln and Asn are subjected to deamination, which can be catalyzed by the residues Thr and Ser (Wright, 1991). This means that Gln and Asn are weak links in the protein structure due to their tendency to deamination which can lead to the cleavage of the chain, particularly at temperatures approaching or exceeding 90° C. It seems probable that these weak links are protected or eliminated in these thermostable proteins. On average, the neutralization of these weak points leads to an overall reduction in the number of these residues in the hyperthermostable sequences, as statistical analyses show (Szilagyi and Zavodszky, 2000).

Moreover, the sequence of the PTE of *S. solfataricus* shows an increase in the content of charged amino acids. It contains 77 (24.5% of the total residues) charged residues Asp, Glu, Lys or Arg, while the two mesophilic PTEs contain 69 of them (approximately 21% of the total residues). The three-dimensional structure shows that the greater part of these charged residues is located on the surface of the protein, which is consistent with previous observations (Szilagyi and Zavodszky, 2000) on hyperthermostable proteins. These descriptions reflect the great differences between the proportions of charged residues and non-charged residues in these types of proteins, as has already been deduced by comparisons of the whole genome of hyperthermophilic and mesophilic organisms (Fukuchi and Nishikawa, 2001).

1.4 Electrostatic Interactions

Analyses of the total number of hydrogen bonds using HBPLUS did not show significant differences between mesophilic PTEs and the hyperthermostable protein. By contrast, the difference in stability between these proteins is certainly partly due to the large number of salt bridges observed for the PTE of *S. solfataricus*, compared with mesophilic proteins. Salt bridges are described as dominant elements in the structures of hyperthermophilic proteins as they contribute to the thermodynamic stability of the proteins (Sterner and Liebl, 2001). Thus, in parallel with an increase in the thermostability of the proteins, these salt bridges have a tendency to arrange themselves in networks of charges which are usually found on the surface of the protein (Vieille C., 1996) as observed in this structure. A high level of cooperation between the ionic bonds seems more effective for thermostability than a sum of isolated ion pairs.

The presence of this large number of salt bridges and their arrangement in networks seem insufficient in themselves to explain the incredible thermostability of the PTE of *S. solfataricus*. In fact, the increase in the number of salt bridges between the hyperthermophilic TIMs and their mesophilic homologues has only been described for the TIM bacteria of *Thermotoga maritima*. This strategy is probably not the only one for achieving thermostability given that not all the archaeal TIMs previously described used ionic bonds as a means of thermostabilization. The PTE of *S. solfataricus* is, as far as we know, the first archaeal TIM which possesses a significantly greater number of salt bridges than its mesophilic homologues.

Proteins adapt to extreme conditions by preserving their functional state, which is characterized by a subtle balance between stability and flexibility. Given that this balance is based on a few hydrogen bonds, salt bridges, hydrophobic interactions or shortening of loops, thermostabilization is clearly achieved by accumulating numerous and subtle improvements at different sites of the protein (Jaenicke, R. 1996). It is also proposed that at ambient temperature the thermostable enzymes are less flexible than their mesophilic homologues; on the other hand the two enzymes display an equivalent flexibility at their optimum activity temperature.

The crystallographic structure of the PTE of *S. solfataricus* shows that its increased rigidity is caused by a certain number of specific structural differences compared with its mesophilic homologues. Possible factors determining its thermostability are deletions and stabilizations of flexible regions; compaction and reinforcement of the dimer; and an increased number of pairs of ions which are partly arranged in networks of charges.

2. The Active Site 2.1 Biological Implication

Several OP hydrolases have been isolated and characterized. The one that is best known is PTE which was originally isolated from soil bacteria. However, the natural substrate of these enzymes remains unknown. As the synthesis of the most effective substrate determined to date, namely paraoxon, was described for the first time in 1950, there are a few controversies about the origin of this activity. In fact, it could be an activity due to a structural proximity of the substrate, or these enzymes could have evolved specifically against these molecules over this short period of time.

With regard to the PTE of *S. solfataricus*, it seems unlikely that this protein would have evolved specifically to hydrolyze these insecticides because these molecules occur very little in the biotope of this archaeon. Moreover, its environment (approximately 90° C.) would lead to an extremely rapid spontaneous degradation of these thermolabile compounds.

The structure of this enzyme also displays a hydrophobic tunnel which communicates with the active site. This tunnel, which is rather narrow, could be an indication of physiological substrates such as N-acyl L-homoserine lactones. Moreover, this fact would be consistent with the discovery of this gene in the centre of a lipase cluster (Merone et al., 2005). The presence of this type of hydrophobic tunnel is standard for this type of substrate and has already been described (Musayev et al., 2005). Despite three prolines, the loop of nine residues at the origin of the tunnel seems more flexible than the remainder of the protein, with an average thermal agitation factor of 48 $\text{Å}^2$. This suggests that this loop is sufficiently flexible to adapt to the fixation of a substrate, and sufficiently rigid to position the latter correctly.

The three-dimensional structure also reveals the presence of a cysteine residue in the cavity of the active site. This is interesting because this type of residue, with Met, Asn and Gln, is considered as a thermolabile amino acid for hyperthermophilic proteins. Generally, their number is drastically reduced in these proteins (Sterner and Liebl, 2001), as is described for Asn and Gln in this study. Cys 258 is very accessible to the solvent. The crystalline structure does not show a particular activation of this residue. However, knowing the reactivity of this cysteine would be useful for establishing the physiological role of this enzyme.

2.2 Proposed Novel Mechanism

Based on the mechanism suggested by Aubert et al. (2004), we propose for this new hyperthermophilic PTE a novel mechanism for the activated hyperthermophilic PTE which does not involve the proton transfer previously described.

The bimetallic centre is used to activate the substrate for a nucleophilic attack by polarizing the phosphorus-oxygen bond. The oxygen of the phosphorus binds to the β metal, which increases the electrophilic character of the phosphorus centre and facilitates the nucleophilic attack of the hydroxide ion. In fact, the binding of the oxygen borne by the phosphorus to the β metal could have increased the reactivity of the water molecule by weakening the interaction of the latter on the β metal.

When the substrate is complexed to this bimetallic centre, the hydroxide ion attacks the phosphorus centre via an SN2 type mechanism, which causes the formation of a pentavalent intermediate which bridges the two metals. The negative charge which develops on the oxygen of the phosphorus is stablized by the interaction with the metals, particularly the β metal. The pair of electrons of this oxygen folds over the phosphorus-oxygen bond, allowing the departure of the leaving group. The phosphorus-containing product which bridges the two metals is evacuated from the active site by a new water molecule of the solvent. This phosphorus-containing molecule is deprotonated by the solvent molecule via its pKa. Aubert et al. (2004) suggest the existence of a proton transfer in the mechanism of the PTE of *P. diminuta*. Briefly, in this mechanism, Asp 301 is assumed to take the proton of the pentavalent intermediate. The proton is then evacuated from the active site with the assistance of His 254 and Asp 233. We do not think that this could be produced for the PTE of *S. solfataricus*, because the residue corresponding to His 254 is an arginine. This arginine interacts with Asp 256 via its NE, which makes any proton transfer more difficult in the mechanism of the PTE of *S. solfataricus*.

This novel mechanism is in fact general to all the PTEs characterized. Certain indications in fact contradict the mechanism of Aubert et al. The PTE of *A. radiobacter* is a very active enzyme and it also possesses an arginine at this position. Moreover, mutagenesis work carried out on the PTE of *P. diminuta* confirms our hypothesis. The H254R and H254G mutations do not display drastic effects on the catalytic parameters of the enzyme (Grimsley et al., 2005; Hill et al., 2003).

Other inconsistencies can also be noted. In the PTE of *P. diminuta*, Asp 301 is in very close interaction with the α metal. From an electrostatic point of view this implies that this negatively charged residue does not have to be protonated. Moreover, the two nitrogens of the imidazole of His 254 are in hydrogen bonds with negatively charged residues (Asp 301 and Asp 233). The effect of this must be to increase the pKa of this histidine, which favours the imidazolium form, and suggests that this residue is not in the best environment to carry out the acid/base catalysis proposed in this proton transfer.

In conclusion, the analysis of this structure made it possible to find elements explaining the incredible thermostability of this enzyme. Moreover, the analysis of this structure as well as an important bibliographical work made it possible to propose a novel general action mechanism for all PTEs.

Finally, all these analyses allow the rapid development of biocatalysts according to the protocol described hereafter.

II) Method for the Preparation of Mutated Hyperthermophilic Phosphotriesterases with a Lactonase Activity According to the Invention, Derived from the Hyperthermophilic PTE of *Sulpholobus solfataricus* Corresponding to the Sequence SEQ ID NO: 3, In order to prepare the synthetic gene Ssopox with 945 base pairs (bp) Ssopox encoding the mutated hyperthermophilic phosphotriesterases with a lactonase activity according to the invention, derived from the hyperthermophilic PTE of *Sulpholobus solfataricus* corresponding to the sequence SEQ ID NO: 3, and comprising at least one of the following four mutations:

substitution of the tyrosine Y in position 97 by a tryptophan W,
substitution of the tyrosine Y in position 99 by a phenylalanine F,
substitution of the arginine R in position 223 by a histidine H,
substitution of the cysteine C in position 258 by a leucine L, and, if appropriate, at least one of the following mutations:

substitution of the valine V in position 27 by an alanine A,
substitution of the proline P in position 67 by a valine V,
substitution of the threonine T in position 68 by a serine S,
substitution of the leucine L in position 72 by an isoleucine I,
substitution of the aspartate D in position 141 by a threonine T,
substitution of the glycine G in position 225 by a proline P,
substitution of the leucine L in position 226 by a histidine H,
substitution of the phenylalanine F in position 229 by a serine S,
substitution of the tryptophan W in position 263 by an alanine A,
substitution of the tryptophan W in position 278 by an isoleucine I, 14 oligonucleotides (7 sense and 7 antisense) were used. The size of the oligonucleotides was approximately 90 pb, and each primer overlaps the next by an overlapping region of 27 pb. The oligonucleotidic sequences in question in the direction 5'-3' are as follows:

```
1for:                                    (SEQ ID NO: 18)
GATATACATATGAGAATACCATTAGTTGGGAAAGATTCAATAGAATCTAA
GGACATAGGATTTACGCTAATTCATGAACATTTAAGAGcTTTTA
GCGAAGCG 2rev:                                    (SEQ ID NO: 19)
AACCTCATTTACAGCGTTTCTGAACTCCTCATCTTCGTTATATAGATGGG
CCATTGTTGTCTGACCGCTTCGCTAAAAGCTCTTAAATGTTC 3for:                                    (SEQ ID NO: 20)
GAGTTCAGAAACGCTGTAAATGAGGTTAAAAGGGCAATGCAATTTGGAGT
AAAGACTATAGTAGATgtCtCTGTAATGGGAaTtGGTAGGGAC 4rev:                                    (SEQ ID NO: 21)
CGTCCCCGCAACTAAATTTATCCCGGTAGCCTTAACCACTTTTTCCATAA
ATCTGATGTCCCTACCAATTCCCATTACAGAGACATCTACTAT 5for:                                    (SEQ ID NO: 22)
ACCGGGATAAATTTAGTTGCGGGGACGGGGATTTggATATtTATCGACTT
ACCTTTCTATTTCTTAAATAGGTCAATTGATGAGATAGCTGAC 6rev:                                    (SEQ ID NO: 23)
TATCTTTACGAAGCCAGCTTTATTGAGAGTACCTTGTATTCCCTCTTTTA
TATCATGAATAAACAAGTCAGCTATCTCATCAATTGACCTATT 7for:                                    (SEQ ID NO: 24)
CTCAATAAAGCTGGCTTCGTAAAGATAGCTGCAacTGAACCTGGGATCAC
AAAGGATGTGGAGAAGGTAATAAGGGCTGCTGCCATAGCAAAC
```

-continued

```
8rev:                                      (SEQ ID NO: 25)
TTGCTGTTCTAATCCGGTGTTATTGTGAGCGTTAGAGTGGGTAATTATTG
GTACTTTAGTCTCTTTGTTTGCTATGGCAGCAGCCCTTATTAC 9for:                                      (SEQ ID NO: 26)
CACAATAACACCGGATTAGAACAGCAAAGAATATTGACTGAAGAAGGTGT
TGATCCAGGGAAAATATTAATAGGTCATTTAGGTGATACAGAT 10rev:                                     (SEQ ID NO: 27)
AggAaAatgATCTAATCCAATAAAGGATCCCTTATCTGCTATCTTCTTTA
TGTAATCTATATTATCTGTATCACCTAAATGACCTATTAA 11for:                                     (SEQ ID NO: 28)
TCCTTTATTGGATTAGATcatTtTccTcatGATTTATcCCTACCTGTTGA
TAAGAGAAATGAAACGACCTTAAGACTAATCAAAGATGGTTATTCAGAT 12rev:                                     (SEQ ID NO: 29)
tttatattctggttttgcagttccagcgtcGAatgtgcataAataatcgt
gagagatcattatcttatctgaataaccatctttgattagtct 13for:                                     (SEQ ID NO: 30)
gctGGAACTGCAAAACCAGAATATAAACCTAAGCTTGCTCCAAGAattAG
TATAACTCTAATATTTGAGGATACGATACCGTTCTTAAAGAGA 14rev:                                     (SEQ ID NO: 31)
CAACCCGAATTCTTAGCTGAAGAACTTTTTCGGATTTTCCTTAAATATTG
TAGCTATAACCTCTTCATTCATTCACTCCATTTCTCTTTAAGAACGGTAT
CGTATCCTC
```

The nucleotides chosen to carry out the mutations in the protein are shown in bold and the overlapping regions are underlined. The oligonucleotides 1 for and 14 rev were also constructed so as to insert the restriction sites NdeI and EcoRI into the N-terminal and C-terminal sequences of the gene respectively.

The oligonucleotides were purified by acrylamide gel electophoresis (10%) according to the method described in Sambrook (Sambrook J. and Russell D. W. 2001 "Molecular Cloning: a laboratory manual").

The reconstruction method of the gene essentially comprises 4 stages. In the first stage, successive pairs of oligonucleotides (for example 1 for with 2 rev) are mixed (at a final concentration of 200 nM) in a PCR tube with a polymerase 1× DeepVent buffer (NEB), 6 mM $MgSO_4$, 200 uM dNTP and 1 U of Polymerase DeepVent, and placed in a thermal cycle apparatus in order to obtain fragments of approximately 160 pb (cycle: 10 mM at 95° C., 1 min at 68° C., 10 mM at 72° C.). The fragments obtained are mixed (at a concentration of 20 nM), then digested with DnaseI (0.0013 U; 30 s-1.5 min at ambient temperature. The DnaseI reaction is stopped by thermal deactivation at 95° C. for 10 minutes. The third stage, or assembly stage, is a PCR (1 mM 95° C., 30 sec 50° C., 30 sec 72° C., 55 times) in order to combine the fragments obtained after digestion with DnaseI and reconstruct the whole Ssopox gene, without the addition of external oligos.

In the last stage, or amplification stage, the external oligonucleotides (5' sense and 3' antisense ssopox; Merone et al., 2005) are added to the mixture, at a final concentration of 1 μM, in order to amplify the whole gene (PCR cycle: 1 min at 95° C., 30 sec at 50° C., 30 sec at 72° C.).

A fragment of approximately 950 pb can be detected by passing an aliquot over 1% agarose gel. The DNA is purified and cloned in a plasmid for sequencing.

BIBLIOGRAPHY

AFRIAT, L., ROODVELDT, C., MANCO, G. & TAWFIK, D. S. (2006).
The latent promiscuity of newly identified microbial lactonases is linked to a recently diverged phosphotriesterase.
Biochemistry 45, 13677-13686.
AUBERT SD., LI Y., RAUSHEL F M.
Mechanism for the hydrolysis of organophosphates by the bacterial phosphotriesterase.
Biochemistry. 2004, 43: 5707-15.
BENNING M M., KUO J M., RAUSHEL F M., HOLDEN H M.
Three-dimensional structure of phosphotriesterase: an enzyme capable of detoxifying organophosphate nerve agents.
Biochemistry. 1994, 33: 15001-7.
BENNING M M., KUO J M., RAUSHEL F M., HOLDEN H M.
Three-dimensional structure of the binuclear metal center of phosphotriesterase.
Biochemistry. 1995, 34: 7973-8.
BENNING M M., SHIM H., RAUSHEL F M., HOLDEN H M.
High resolution X-ray structures of different metal-substituted forms of phosphotriesterase from *Pseudomonas* diminuta.
Biochemistry. 2001, 40: 2712-22
CHEN-GOODSPEED M, SOGORB M A., WU F, HONG S B & RAUSHEL F M.
Structural determinants of the substrate and stereochemical specificity of phosphotriesterase.
Biochemistry, 2001, 40, 1325-31
DONG, Y. H., GUSTI, A. R., ZHANG, Q., XU, J. L. & ZHANG, L. H. (2002).
Identification of quorum-quenching N-acyl homo serine lactonases from *Bacillus* species.
Appl Approximately Microbiol 68, 1754-1759.
DONG, Y. H., WANG, L. H., XU, J. L., ZHANG, H. B., ZHANG, X. F. & ZHANG, L. H. (2001). Quenching quorum-sensing-dependent bacterial infection by an N-acyl homo serine lactonase. Nature 411, 813-817.
DONG, Y. H., XU, J. L., LI, X. Z. & ZHANG, L. H. (2000).
AiiA, an enzyme that inactivates the acylhomoserine lactone quorum-sensing signal and attenuates the virulence of *Erwinia* carotovora.
Proceedings of the National Academy of Sciences of the United States of America 97, 3526-3531.
ELIAS, M., DUPUY, J., MERONE, L., LECOMTE, C., ROSSI, M., MASSON, P., MANCO, G. & CHABRIERE, E. (2007a).
Crystallization and preliminary X-ray diffraction analysis of the hyperthermophilic *Sulfolobus solfataricus* phosphotriesterase.
Acta Crystallograph Sect F Struct Biol Cryst Commun 63, 553-555.
ELIAS, M., DUPUY, J., MERONE, L., MANDRICH, L., PORZIO, E., MONIOT, S., ROCHU, D., LECOMTE, C., ROSSI, M., MASSON, P., ET AL. (2007b).
Structural basis for natural lactonase and promiscuous phosphotriesterase activities. submitted.
FEDERLE, M. J. & BASSLER, B. L. (2003).
Interspecies communication in bacteria.
The Journal of clinical investigation 112, 1291-1299.
FUKUCHI S., NISHIKAWA K.
Protein surface amino acid compositions distinctively differ between thermophilic and mesophilic bacteria.
J. Mol. Biol. 2001, 309: 835-43.
FUQUA, C. & GREENBERG, E. P. (2002).
Listening in on bacteria: acyl-homoserine lactone signalling.
Nature reviews 3, 685-695.
GRIMSLEY J K., CALAMINI B., WILD J R., MESECAR A D.

Structural and mutational studies of organophosphorus hydrolase reveal a cryptic and functional allosteric-binding site.
Arch Biochem Biophys. 2005, 442:169-79.
HAREL M., AHARONI A., GAIDUKOV L., BRUMSHTEIN B., KHERSONSKY O., MEGED R., DVIR H., RAVELLI R B., McCARTHY A., TOKER L., SILMAN I., SUSSMAN J L. & TAWFIK D S. Structure and evolution of the serum paraoxonase family of detoxifying and anti-atherosclerotic enzymes. Nat. Struct. Mol. Biol. 2004, 11:412-9.
HILL C M., LI W S., THODEN J B., HOLDEN H M., RAUSHEL F M.
Enhanced degradation of chemical warfare agents through molecular engineering of the phosphotriesterase active site.
J. Am. Chem. Soc. 2003, 125: 8990-1.
JACKSON C J., CARR P D., KIM H K., LIU J W., HERRALD P., MITIC N., SCHENK G., SMITH C A, OLLIS D L.
Anomalous scattering analysis of *Agrobacterium* radiobacter phosphotriesterase: the prominent role of iron in the heterobinuclear active site.
Biochem. J. 2006 May 11
JACKSON C J., LIU J W., COOTE M L., OLLIS D L.
The effects of substrate orientation on the mechanism of a phosphotriesterase.
Org. Biomol. Chem. 2005, 3: 4343-50.
JAENICKE R.
Glyceraldehyde-3-phosphate dehydrogenase from *Thermotoga maritima*: strategies of protein stabilization.
FEMS Microbiol Rev. 1996, 18: 215-24.
LIN, Y. H., XU, J. L., HU, J., WANG, L. H., ONG, S. L., LEADBETTER, J. R. & ZHANG, L. H.
Acyl-homoserine lactone acylase from Ralstonia strain XJ12B represents a novel and potent class of quorum-quenching enzymes.
Molecular microbiology 47, 849-860 (2003).
LO CONTE L., CHOTHIA C., JANIN J.
The atomic structure of protein-protein recognition sites.
J. Mol. Biol. 1999, 285: 2177-98.
MERONE L., MANDRICH L., ROSSI M., MANCO G.
A thermostable phosphotriesterase from the archaeon *Sulfolobus solfataricus*: cloning, overexpression and properties.
Extremophiles. 2005, 9: 297-305.
MERONE, L., MANDRICH, L., ROSSI, M. & MANCO, G.
A thermostable phosphotriesterase from the archaeon *Sulfolobus solfataricus*: cloning, overexpression and properties.
Extremophiles 9 (2005), 297-305.
MUNNECKE D M.
Enzymatic hydrolysis of organophosphate insecticides, a possible pesticide disposal method.
Appl. Environ. Microbiol. 1976, 32:7-13.
MUSAYEV F., SACHDEVA S., SCARSDALE J N., REYNOLDS K A., WRIGHT H T.
Crystal structure of a substrate complex of *Mycobacterium tuberculosis* beta-ketoacyl-acyl carrier protein synthase III (FabH) with lauroyl-coenzyme
A. J. Mol. Biol. 2005, 346: 1313-21.
OH, K. B., MIYAZAWA, H., NAITO, T. & MATSUOKA, H. (2001).
Purification and characterization of an autoregulatory substance capable of regulating the morphological transition in *Candida albicans*.
Proceedings of the National Academy of Sciences of the United States of America 98, 4664-4668.
PASSADOR, L., COOK, J. M., GAMBEILO, M. J., RUST, L. & IGLEWSKI, R H.
Expression of *Pseudomonas aeruginosa* virulence genes requires cell-to-cell communication.
Science (New York, N.Y.) 260, 1127-1130 (1993).
PIRHONEN, M., FLEGO, D., HEIKINHEIMO, R. & PALVA, E. T.
A small diffusible signal molecule is responsible for the global control of virulence and exoenzyme production in the plant pathogen *Erwinia carotovora*.
The EMBO journal 12 (1993), 2467-2476.
PORZIO E. MERONE L. MANDRICH L. ROSSI M. MANCO G.
A new phosphotriesterase from *Sulfolobus acidocaldarius* and its comparison with the homologue from *Sulfolobus solfataricus*.
Biochimie 2007
RASMUSSEN, T. B. & GIVSKOV, M.
Quorum-sensing inhibitors as anti-pathogenic drugs.
Int J Med Microbiol 296, 149-161 (2006).
RAVEH L., GRUNWALD J., MARCUS D., PAPIER Y., COHEN E., ASHANI Y.
Human butyrylcholinesterase as a general prophylactic antidote for nerve agent toxicity. In vitro and in vivo quantitative characterization.
Biochem. Pharmacol., 1993, 45:2465-74
REIMMANN, C., GINET, N., MICHEL, L., KEEL, C., MICHAUX, P., KRISHNAPILLAI, V., ZALA, M., HEURLIER, K., TRIANDAFILLU, K., HARMS, H., ET AL.
Genetically programmed autoinducer destruction reduces virulence gene expression and swarming motility in *Pseudomonas aeruginosa* PAO1.
Microbiology (Reading, England) 148, 923-932 (2002).
SAMPLES C R., HOWARD T., RAUSHEL F M., DeROSE V J.
Protonation of the binuclear metal center within the active site of phosphotriesterase.
Biochemistry. 2005, 44:11005-13.
STERNER R, LIEBL W.
Thermophilic adaptation of proteins. Crit. Rev. Biochem. Mol. Biol. 2001, 36:39-106.
SZILAGYI A., ZAVODSZKY P.
Structural differences between mesophilic, moderately thermophilic and extremely thermophilic protein subunits: results of a comprehensive survey.
Structure. 2000, 8: 493-504.
VANHOOKE J L., BENNING M M., RAUSHEL F M., HOLDEN H M.
Three-dimensional structure of the zinc-containing phosphotriesterase with the bound substrate analog diethyl 4-methylbenzylphosphonate.
Biochemistry. 1996; 35:6020-5.
VIEILLE C. & ZEIKUS G J.
Hyperthermophilic enzymes: sources, uses, and molecular mechanisms for thermostability.
Microbiol Mol Biol Rev. 2001, 65:1-43.
VIEILLE C., BURDETTE D S., ZEIKUS J G.
Thermozymes.
Biotechnol Annu Rev. 1996, 2:1-83.
WALDEN H. TAYLOR G L., LORENTZEN E., POHL E., LILIE H., SCHRAMM A., KNURA T., STUBBE K., TJADEN B., HENSEL R.

Structure and function of a regulated archaeal triosephosphate isomerase adapted to high temperature.
J. Mol. Biol. 2004, 342: 861-75.
WHITEHEAD, N. A., BARNARD, A. M., SLATER, H., SIMPSON, N. J. & SALMOND, A. P.
Quorum-sensing in Gram-negative bacteria.
FEMS microbiology reviews 25, 365-404 (2001).
WRIGHT HT.

Sequence and structure determinants of the nonenzymatic deamidation of asparagine and glutamine residues in proteins.
Protein Eng. 1991, 4: 283-94.
ZHANG, L. H.
Quorum quenching and proactive host defense.
Trends in plant science 8, 238-244 (2003).

The invention claimed is:

1. A purified mutated hyperthermophilic phosphotriesterase (PTE) having a lactonase activity derived from a hyperthermophilic PTE corresponding to the consensus sequence of SEQ ID NO: 1, said mutated PTE comprising at least one mutation selected from the group consisting of:

substitution of the tyrosine Y in position 98,
substitution of the tyrosine Y in position 100,
substitution of the arginine R in position 224, and
substitution of the cysteine C in position 259,
of SEQ ID NO: 1 by any other natural or non-natural amino acid, said mutated hyperthermophilic PTE having a lactonase activity that is greater than that of a non-mutated hyperthermophilic PTE from which it is derived.

2. The mutated hyperthermophilic PTE according to claim 1, derived from the hyperthermophilic PTE of *Sulfolobus solfataricus* corresponding to the sequence SEQ ID NO: 3, or from the hyperthermophilic PTE of *Sulfolobus acidocaldarius* corresponding to the sequence SEQ ID NO: 5, said sequences SEQ ID NO: 3 and SEQ ID NO: 5 belonging to the consensus sequence SEQ ID NO: 1, the amino acid in position 2 in SEQ ID NO: 1 being missing from SEQ ID NO: 3.

3. The mutated hyperthermophilic PTE according to claim 1, comprising at least the following four mutations:
   substitution of the tyrosine Y in position 98,
   substitution of the tyrosine Y in position 100,
   substitution of the arginine R in position 224, and
   substitution of the cysteine C in position 259,
of SEQ ID NO: 1 by any other natural or non-natural amino acid.

4. The mutated hyperthermophilic PTE according to claim 1, further comprising at least one mutation selected from the group consisting of:
   substitution of the valine V in position 28,
   substitution of the proline P in position 68,
   substitution of the threonine T in position 69,
   substitution of the leucine L in position 73,
   substitution of the aspartate D in position 142,
   substitution of the glycine G in position 226,
   substitution of the leucine L in position 227,
   substitution of the phenylalanine F in position 230,
   substitution of the tryptophan W in position 264, and
   substitution of the tryptophan W in position 279,
of SEQ ID NO: 1 by any other natural or non-natural amino acid.

5. The mutated hyperthermophilic PTE according to claim 1, further comprising the following five mutations:
   substitution of the valine V in position 28,
   substitution of the leucine L in position 73,
   substitution of the aspartate D in position 142,
   substitution of the glycine G in position 226, and
   substitution of the leucine L in position 227,
of SEQ ID NO: 1 by any other natural or non-natural amino acid.

6. The mutated hyperthermophilic PTE according to claim 1, further comprising the following five mutations:
   substitution of the proline P in position 68,
   substitution of the threonine T in position 69,
   substitution of the phenylalanine F in position 230,
   substitution of the tryptophan W in position 264, and
   substitution of the tryptophan W in position 279,
of SEQ ID NO: 1 by any other natural or non-natural amino acid.

7. The mutated hyperthermophilic PTE according to claim 1, wherein the at least one mutation is selected from the group consisting of:
   substitution of the tyrosine Y in position 98 by a tryptophan W,
   substitution of the tyrosine Y in position 100 by a phenylalanine F,
   substitution of the arginine R in position 224 by a histidine H, and
   substitution of the cysteine C in position 259 by a leucine L.

8. The mutated hyperthermophilic PTE according to claim 1, derived from the hyperthermophilic PTE of *Sulfolobus solfataricus* corresponding to the sequence SEQ ID NO: 3, and comprising at least one mutation selected from the group consisting of:
   substitution of the tyrosine Y in position 97,
   substitution of the tyrosine Y in position 99,
   substitution of the arginine R in position 223, and
   substitution of the cysteine C in position 258,
of SEQ ID NO: 3 by any other natural or non-natural amino acid.

9. The mutated hyperthermophilic PTE according to claim 8, comprising at least the following four mutations:
   substitution of the tyrosine Y in position 97,
   substitution of the tyrosine Y in position 99,
   substitution of the arginine R in position 223, and
   substitution of the cysteine C in position 258,
of SEQ ID NO: 3 by any other natural or non-natural amino acid.

10. The mutated hyperthermophilic PTE according to claim 8, further comprising at least one mutation selected from the group consisting of:
    substitution of the valine V in position 27,
    substitution of the proline P in position 67,
    substitution of the threonine T in position 68,
    substitution of the leucine L in position 72,
    substitution of the aspartate D in position 141,
    substitution of the glycine G in position 225,
    substitution of the leucine L in position 226,
    substitution of the phenylalanine F in position 229,
    substitution of the tryptophan W in position 263, and
    substitution of the tryptophan W in position 278,
of SEQ ID NO: 3 by any other natural or non-natural amino acid.

11. The mutated hyperthermophilic PTE according to claim 8, comprising the following five mutations:
    substitution of the valine V in position 27,
    substitution of the leucine L in position 72,
    substitution of the aspartate D in position 141,
    substitution of the glycine G in position 225, and
    substitution of the leucine L in position 226,
of SEQ ID NO: 3 by any other natural or non-natural amino acid.

12. The mutated hyperthermophilic PTE according to claim 8, comprising the following five mutations:
    substitution of the proline P in position 67,
    substitution of the threonine T in position 68,
    substitution of the phenylalanine F in position 229,
    substitution of the tryptophan W in position 263, and
    substitution of the tryptophan W in position 278,
of SEQ ID NO: 3 by any other natural or non-natural amino acid.

13. The mutated hyperthermophilic PTE according to claim 8, comprising at least one mutation selected from the group consisting of:
    substitution of the tyrosine Y in position 97 by a tryptophan W,
    substitution of the tyrosine Y in position 99 by a phenylalanine F,
    substitution of the arginine R in position 223 by a histidine H, and
    substitution of the cysteine C in position 258 by a leucine.

14. The mutated hyperthermophilic PTE according to claim 8, comprising:
    SEQ ID NO: 7, corresponding to SEQ ID NO: 3 comprising the following four mutations:
        substitution of the tyrosine Y in position 97 by a tryptophan W,
        substitution of the tyrosine Y in position 99 by a phenylalanine F,
        substitution of the arginine R in position 223 by a histidine H, substitution of the cysteine C in position 258 by a leucine L, SEQ ID NO: 9, corresponding to SEQ ID NO: 7 additionally comprising the following five mutations:
substitution of the valine V in position 27 by an alanine A,
substitution of the leucine L in position 72 by an isoleucine I,
substitution of the aspartate D in position 141 by a threonine T,
substitution of the glycine G in position 225 by a proline P,
substitution of the leucine L in position 226 by a histidine H, or SEQ ID NO: 11, corresponding to SEQ ID NO: 9 additionally comprising the following five mutations:
substitution of the proline P in position 67 by a valine V,
substitution of the threonine T in position 68 by a serine S,
substitution of the phenylalanine F in position 229 by a serine S,
substitution of the tryptophan W in position 263 by an alanine A,
substitution of the tryptophan W in position 278 by an isoleucine I.

15. The mutated hyperthermophilic PTE according to claim 8, comprising at least one mutation corresponding to a substitution of at least one of the amino acids of the following amino acid pairs, the positions of which in SEQ ID NO: 3 are indicated hereafter, by another natural or non-natural amino acid: 2R/314S, 14K/12E, 26R/75D, 26R/42E, 33R/42E, 33R/45E, 55R/52E, 55R/285E, 74R/121D, 81K/42E, 81K/43D, 84K/80E, 109R/113E, 123K/162E, 147K/148D, 151K/148D, 154R/150E, 154R/187E, 154R/188E, 161K/188E, 183R/150E, 183R/187E, 183R/180E, 210K/245D, 215K/214D, 223R/256D, 223R/202D, 234K/204D, 235R/202D, 241R/245D, 245D/244K, 250K/249D, 277R/286D, 292K/298E, and 310K/307E.

16. The mutated hyperthermophilic PTE according to claim 1, derived from the hyperthermophilic PTE of *Sulfolobus acidocaldarius* corresponding to the sequence SEQ ID NO: 5, and comprising at least one mutation selected from the group consisting of:
substitution of the tyrosine Y in position 98,
substitution of the tyrosine Y in position 100,
substitution of the arginine R in position 224, and
substitution of the cysteine C in position 259,
of SEQ ID NO: 5 by any other natural or non-natural amino acid.

17. The mutated hyperthermophilic PTE according to claim 16, comprising at least the following four mutations:
substitution of the tyrosine Y in position 98,
substitution of the tyrosine Y in position 100,
substitution of the arginine R in position 224, and
substitution of the cysteine C in position 259,
of SEQ ID NO: 5 by any other natural or non-natural amino acid.

18. The mutated hyperthermophilic PTE according to claim 16, further comprising at least one mutation selected from the group consisting of:
substitution of the valine V in position 28,
substitution of the proline P in position 68,
substitution of the threonine T in position 69,
substitution of the leucine L in position 73,
substitution of the aspartate D in position 142,
substitution of the glycine G in position 226,
substitution of the leucine L in position 227,
substitution of the phenylalanine F in position 230,
substitution of the tryptophan W in position 264, and
substitution of the tryptophan W in position 279,
of SEQ ID NO: 5 by any other natural or non-natural amino acid.

19. The mutated hyperthermophilic PTE according to claim 16, comprising the following five mutations:
substitution of the valine V in position 28,
substitution of the leucine L in position 73,
substitution of the aspartate D in position 142,
substitution of the glycine G in position 226, and
substitution of the leucine L in position 227,
of SEQ ID NO: 5 by any other natural or non-natural amino acid.

20. The mutated hyperthermophilic PTE according to claim 16, comprising the following five mutations:
substitution of the proline P in position 68,
substitution of the threonine T in position 69,
substitution of the phenylalanine F in position 230,
substitution of the tryptophan W in position 264, and
substitution of the tryptophan W in position 279,
of SEQ ID NO: 5 by any other natural or non-natural amino acid.

21. The mutated hyperthermophilic PTE according to claim 16, comprising at least one mutation selected from the group consisting of:
substitution of the tyrosine Y in position 98 by a tryptophan W,
substitution of the tyrosine Y in position 100 by a phenylalanine F,
substitution of the arginine R in position 224 by a histidine H, and
substitution of the cysteine C in position 259 by a leucine L.

22. The mutated hyperthermophilic PTE according to claim 16, comprising:
SEQ ID NO: 13, corresponding to the sequence SEQ ID NO: 5 comprising the following four mutations:
substitution of the tyrosine Y in position 98 by a tryptophan W,
substitution of the tyrosine Y in position 100 by a phenylalanine F,
substitution of the arginine R in position 224 by a histidine H,
substitution of the cysteine C in position 259 by a leucine L, SEQ ID NO: 15, corresponding to the sequence SEQ ID NO: 13 additionally comprising the following five mutations:
substitution of the valine V in position 28 by an alanine A,
substitution of the leucine L in position 73 by an isoleucine I,
substitution of the aspartate D in position 142 by a threonine T,
substitution of the glycine G in position 226 by a proline P,
substitution of the leucine L in position 227 by a histidine H, or SEQ ID NO: 17, corresponding to the sequence SEQ ID NO: 15 additionally comprising the following five mutations:
substitution of the proline P in position 68 by a valine V,
substitution of the threonine T in position 69 by a serine S,
substitution of the phenylalanine F in position 230 by a serine S, substitution of the tryptophan W in position 264 by an alanine A, and
substitution of the tryptophan W in position 279 by an isoleucine I.

23. The mutated hyperthermophilic PTE according to claim 1,
wherein at least one amino acid involved in salt bridges is modified by substitution or deletion, such that an activation temperature of said mutated hyperthermophilic PTE is reduced compared with the activation temperature of the mutated hyperthermophilic PTE in which the at least one amino acid involved in the salt bridges is unmodified.

24. An isolated nucleic acid encoding the mutated hyperthermophilic phosphotriesterase (PTE) of claim 1.

25. A vector comprising the nucleic acid according to claim 24.

26. A host cell transformed by the vector according to claim 25.

27. A composition, comprising the mutated hyperthermophilic PTE according to claim 1,
in combination with a pharmaceutically acceptable vehicle.

28. The composition according to claim 27, in a form which can be administered by injectable route or by topical route.

29. The mutated hyperthermophilic PTE according to claim 7, further comprising at least one of the following mutations:
substitution of the valine V at position 28 by an alanine A,
substitution of the proline P at position 68 by a valine V,
substitution of the threonine T at position 69 by a serine S,
substitution of the leucine L at position 73 by an isoleucine I,
substitution of the aspartate D at position 142 by a threonine T,
substitution of the glycine G at position 226 by a proline P,
substitution of the leucine L at position 227 by a histidine H,
substitution of the phenylalanine F at position 230 by a serine S,
substitution of the tryptophan W at position 264 by an alanine A, or
substitution of the tryptophan W at position 279 by an isoleucine I.

30. The mutated hyperthermophilic PTE according to claim 5, comprising the following five mutations:
substitution of the valine V at position 28 by an alanine A,
substitution of the leucine L at position 73 by an isoleucine I,
substitution of the aspartate D at position 142 by a threonine T,
substitution of the glycine G at position 226 by a proline P, and
substitution of the leucine L at position 227 by a histidine H.

31. The mutated hyperthermophilic PTE according to claim 6, comprising the following five mutations:
substitution of the proline P at position 68 by a valine V,
substitution of the threonine T at position 69 by a serine S,
substitution of the phenylalanine F at position 230 by a serine S,
substitution of the tryptophan W at position 264 by an alanine A, and
substitution of the tryptophan W at position 279 by an isoleucine I.

32. The mutated hyperthermophilic PTE according to claim 13, further comprising at least one of the following mutations:
substitution of the valine V at position 27 by an alanine A,
substitution of the proline P at position 67 by a valine V,
substitution of the threonine T at position 68 by a serine S,
substitution of the leucine L at position 72 by an isoleucine I,
substitution of the aspartate D at position 141 by a threonine T,
substitution of the glycine G at position 225 by a proline P,
substitution of the leucine L at position 226 by a histidine H,
substitution of the phenylalanine F at position 229 by a serine S,
substitution of the tryptophan W at position 263 by an alanine A, and
substitution of the tryptophan W at position 278 by an isoleucine I.

33. The mutated hyperthermophilic PTE according to claim 8, comprising the following four mutations:
substitution of the tyrosine Y in position 97 by a tryptophan W,
substitution of the tyrosine Y in position 99 by a phenylalanine F,
substitution of the arginine R in position 223 by a histidine H, and
substitution of the cysteine C in position 258 by a leucine L (SEQ ID NO: 7).

34. The mutated hyperthermophilic PTE according to claim 33, comprising the following five mutations:
substitution of the valine V at position 27 by an alanine A,
substitution of the leucine L at position 72 by an isoleucine I,
substitution of the aspartate D at position 141 by a threonine T,
substitution of the glycine G at position 225 by a proline P, and
substitution of the leucine L at position 226 by a histidine H (SEQ ID NO: 9).

35. The mutated hyperthermophilic PTE according to claim 34, comprising the following five mutations:
substitution of the proline P at position 67 by a valine V,
substitution of the threonine T at position 68 by a serine S,
substitution of the phenylalanine F at position 229 by a serine S,
substitution of the tryptophan W at position 263 by an alanine A, and
substitution of the tryptophan W at position 278 by an isoleucine I (SEQ ID NO: 11).

* * * * *

UNITED STATES PATENT AND TRADEMARK OFFICE
CERTIFICATE OF CORRECTION

PATENT NO.       : 8,372,618 B2
APPLICATION NO. : 12/597847
DATED            : February 12, 2013
INVENTOR(S)      : Chabriere et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 464 days.

Signed and Sealed this
First Day of September, 2015

Michelle K. Lee
*Director of the United States Patent and Trademark Office*

SEQUENCE LISTING

```
<160> NUMBER OF SEQ ID NOS: 31

<210> SEQ ID NO 1
<211> LENGTH: 315
<212> TYPE: PRT
<213> ORGANISM: Sulfobacillus sp.
<220> FEATURE:
<221> NAME/KEY: MISC_FEATURE
<222> LOCATION: (2)..(2)
<223> OTHER INFORMATION: T or blank
<220> FEATURE:
<221> NAME/KEY: MISC_FEATURE
<222> LOCATION: (3)..(3)
<223> OTHER INFORMATION: K or R
<220> FEATURE:
<221> NAME/KEY: MISC_FEATURE
<222> LOCATION: (10)..(10)
<223> OTHER INFORMATION: G or D
<220> FEATURE:
<221> NAME/KEY: MISC_FEATURE
<222> LOCATION: (11)..(11)
<223> OTHER INFORMATION: E or S
<220> FEATURE:
<221> NAME/KEY: MISC_FEATURE
<222> LOCATION: (13)..(13)
<223> OTHER INFORMATION: S or E
<220> FEATURE:
<221> NAME/KEY: MISC_FEATURE
<222> LOCATION: (14)..(14)
<223> OTHER INFORMATION: P or S
<220> FEATURE:
<221> NAME/KEY: MISC_FEATURE
<222> LOCATION: (15)..(15)
<223> OTHER INFORMATION: G or K
<220> FEATURE:
<221> NAME/KEY: MISC_FEATURE
<222> LOCATION: (16)..(16)
<223> OTHER INFORMATION: E or D
<220> FEATURE:
<221> NAME/KEY: MISC_FEATURE
<222> LOCATION: (17)..(17)
<223> OTHER INFORMATION: M or I
<220> FEATURE:
<221> NAME/KEY: MISC_FEATURE
<222> LOCATION: (32)..(32)
<223> OTHER INFORMATION: P or A
<220> FEATURE:
<221> NAME/KEY: MISC_FEATURE
<222> LOCATION: (35)..(35)
<223> OTHER INFORMATION: Y or Q
<220> FEATURE:
<221> NAME/KEY: MISC_FEATURE
<222> LOCATION: (47)..(47)
<223> OTHER INFORMATION: L or F
<220> FEATURE:
<221> NAME/KEY: MISC_FEATURE
<222> LOCATION: (48)..(48)
<223> OTHER INFORMATION: K or R
<220> FEATURE:
<221> NAME/KEY: MISC_FEATURE
<222> LOCATION: (56)..(56)
<223> OTHER INFORMATION: T or R
<220> FEATURE:
<221> NAME/KEY: MISC_FEATURE
<222> LOCATION: (57)..(57)
<223> OTHER INFORMATION: I or A
```

-continued

```
<220> FEATURE:
<221> NAME/KEY: MISC_FEATURE
<222> LOCATION: (59)..(59)
<223> OTHER INFORMATION: S or Q
<220> FEATURE:
<221> NAME/KEY: MISC_FEATURE
<222> LOCATION: (60)..(60)
<223> OTHER INFORMATION: Y or F
<220> FEATURE:
<221> NAME/KEY: MISC_FEATURE
<222> LOCATION: (80)..(80)
<223> OTHER INFORMATION: S or M
<220> FEATURE:
<221> NAME/KEY: MISC_FEATURE
<222> LOCATION: (86)..(86)
<223> OTHER INFORMATION: E or A
<220> FEATURE:
<221> NAME/KEY: MISC_FEATURE
<222> LOCATION: (91)..(91)
<223> OTHER INFORMATION: V or L
<220> FEATURE:
<221> NAME/KEY: MISC_FEATURE
<222> LOCATION: (92)..(92)
<223> OTHER INFORMATION: I or V
<220> FEATURE:
<221> NAME/KEY: MISC_FEATURE
<222> LOCATION: (94)..(94)
<223> OTHER INFORMATION: A or G
<220> FEATURE:
<221> NAME/KEY: MISC_FEATURE
<222> LOCATION: (97)..(97)
<223> OTHER INFORMATION: L or I
<220> FEATURE:
<221> NAME/KEY: MISC_FEATURE
<222> LOCATION: (99)..(99)
<223> OTHER INFORMATION: T or I
<220> FEATURE:
<221> NAME/KEY: MISC_FEATURE
<222> LOCATION: (101)..(101)
<223> OTHER INFORMATION: T or I
<220> FEATURE:
<221> NAME/KEY: MISC_FEATURE
<222> LOCATION: (106)..(106)
<223> OTHER INFORMATION: F or Y
<220> FEATURE:
<221> NAME/KEY: MISC_FEATURE
<222> LOCATION: (108)..(108)
<223> OTHER INFORMATION: N or L
<220> FEATURE:
<221> NAME/KEY: MISC_FEATURE
<222> LOCATION: (109)..(109)
<223> OTHER INFORMATION: G or N
<220> FEATURE:
<221> NAME/KEY: MISC_FEATURE
<222> LOCATION: (112)..(112)
<223> OTHER INFORMATION: L or I
<220> FEATURE:
<221> NAME/KEY: MISC_FEATURE
<222> LOCATION: (113)..(113)
<223> OTHER INFORMATION: E or D
<220> FEATURE:
<221> NAME/KEY: MISC_FEATURE
<222> LOCATION: (117)..(117)
<223> OTHER INFORMATION: E or D
<220> FEATURE:
<221> NAME/KEY: MISC_FEATURE
<222> LOCATION: (119)..(119)
<223> OTHER INFORMATION: L or F
<220> FEATURE:
<221> NAME/KEY: MISC_FEATURE
<222> LOCATION: (125)..(125)
<223> OTHER INFORMATION: K or E
<220> FEATURE:
<221> NAME/KEY: MISC_FEATURE
<222> LOCATION: (131)..(131)
<223> OTHER INFORMATION: N or L
<220> FEATURE:
<221> NAME/KEY: MISC_FEATURE
<222> LOCATION: (133)..(133)
<223> OTHER INFORMATION: R or K
```

```
<220> FEATURE:
<221> NAME/KEY: MISC_FEATURE
<222> LOCATION: (137)..(137)
<223> OTHER INFORMATION: I or V
<220> FEATURE:
<221> NAME/KEY: MISC_FEATURE
<222> LOCATION: (138)..(138)
<223> OTHER INFORMATION: K or X
<220> FEATURE:
<221> NAME/KEY: MISC_FEATURE
<222> LOCATION: (139)..(139)
<223> OTHER INFORMATION: V or I
<220> FEATURE:
<221> NAME/KEY: MISC_FEATURE
<222> LOCATION: (148)..(148)
<223> OTHER INFORMATION: R or K
<220> FEATURE:
<221> NAME/KEY: MISC_FEATURE
<222> LOCATION: (152)..(152)
<223> OTHER INFORMATION: R or K
<220> FEATURE:
<221> NAME/KEY: MISC_FEATURE
<222> LOCATION: (153)..(153)
<223> OTHER INFORMATION: A or V
<220> FEATURE:
<221> NAME/KEY: MISC_FEATURE
<222> LOCATION: (161)..(161)
<223> OTHER INFORMATION: Q or N
<220> FEATURE:
<221> NAME/KEY: MISC_FEATURE
<222> LOCATION: (165)..(165)
<223> OTHER INFORMATION: N or K
<220> FEATURE:
<221> NAME/KEY: MISC_FEATURE
<222> LOCATION: (177)..(177)
<223> OTHER INFORMATION: G or N
<220> FEATURE:
<221> NAME/KEY: MISC_FEATURE
<222> LOCATION: (187)..(187)
<223> OTHER INFORMATION: M or T
<220> FEATURE:
<221> NAME/KEY: MISC_FEATURE
<222> LOCATION: (195)..(195)
<223> OTHER INFORMATION: R or K
<220> FEATURE:
<221> NAME/KEY: MISC_FEATURE
<222> LOCATION: (196)..(196)
<223> OTHER INFORMATION: V or I
<220> FEATURE:
<221> NAME/KEY: MISC_FEATURE
<222> LOCATION: (207)..(207)
<223> OTHER INFORMATION: V or I
<220> FEATURE:
<221> NAME/KEY: MISC_FEATURE
<222> LOCATION: (220)..(220)
<223> OTHER INFORMATION: V or I
<220> FEATURE:
<221> NAME/KEY: MISC_FEATURE
<222> LOCATION: (233)..(233)
<223> OTHER INFORMATION: I or V
<220> FEATURE:
<221> NAME/KEY: MISC_FEATURE
<222> LOCATION: (239)..(239)
<223> OTHER INFORMATION: V or T
<220> FEATURE:
<221> NAME/KEY: MISC_FEATURE
<222> LOCATION: (240)..(240)
<223> OTHER INFORMATION: L or T
<220> FEATURE:
<221> NAME/KEY: MISC_FEATURE
<222> LOCATION: (242)..(242)
<223> OTHER INFORMATION: K or R
<220> FEATURE:
<221> NAME/KEY: MISC_FEATURE
<222> LOCATION: (249)..(249)
<223> OTHER INFORMATION: L or S
<220> FEATURE:
<221> NAME/KEY: MISC_FEATURE
<222> LOCATION: (251)..(251)
<223> OTHER INFORMATION: R or K
```

```
<220> FEATURE:
<221> NAME/KEY: MISC_FEATURE
<222> LOCATION: (254)..(254)
<223> OTHER INFORMATION: V or I
<220> FEATURE:
<221> NAME/KEY: MISC_FEATURE
<222> LOCATION: (256)..(256)
<223> OTHER INFORMATION: Q or H
<220> FEATURE:
<221> NAME/KEY: MISC_FEATURE
<222> LOCATION: (266)..(266)
<223> OTHER INFORMATION: I or T
<220> FEATURE:
<221> NAME/KEY: MISC_FEATURE
<222> LOCATION: (278)..(278)
<223> OTHER INFORMATION: K or R
<220> FEATURE:
<221> NAME/KEY: MISC_FEATURE
<222> LOCATION: (281)..(281)
<223> OTHER INFORMATION: M or I
<220> FEATURE:
<221> NAME/KEY: MISC_FEATURE
<222> LOCATION: (282)..(282)
<223> OTHER INFORMATION: S or T
<220> FEATURE:
<221> NAME/KEY: MISC_FEATURE
<222> LOCATION: (286)..(286)
<223> OTHER INFORMATION: T or E
<220> FEATURE:
<221> NAME/KEY: MISC_FEATURE
<222> LOCATION: (288)..(288)
<223> OTHER INFORMATION: V or T
<220> FEATURE:
<221> NAME/KEY: MISC_FEATURE
<222> LOCATION: (291)..(291)
<223> OTHER INFORMATION: S or F
<220> FEATURE:
<221> NAME/KEY: MISC_FEATURE
<222> LOCATION: (292)..(292)
<223> OTHER INFORMATION: I or L
<220> FEATURE:
<221> NAME/KEY: MISC_FEATURE
<222> LOCATION: (295)..(295)
<223> OTHER INFORMATION: A or N
<220> FEATURE:
<221> NAME/KEY: MISC_FEATURE
<222> LOCATION: (298)..(298)
<223> OTHER INFORMATION: T or N
<220> FEATURE:
<221> NAME/KEY: MISC_FEATURE
<222> LOCATION: (299)..(299)
<223> OTHER INFORMATION: D or E
<220> FEATURE:
<221> NAME/KEY: MISC_FEATURE
<222> LOCATION: (301)..(301)
<223> OTHER INFORMATION: Q or V
<220> FEATURE:
<221> NAME/KEY: MISC_FEATURE
<222> LOCATION: (302)..(302)
<223> OTHER INFORMATION: L or I
<220> FEATURE:
<221> NAME/KEY: MISC_FEATURE
<222> LOCATION: (303)..(303)
<223> OTHER INFORMATION: H or A
<220> FEATURE:
<221> NAME/KEY: MISC_FEATURE
<222> LOCATION: (304)..(304)
<223> OTHER INFORMATION: V or T
<220> FEATURE:
<221> NAME/KEY: MISC_FEATURE
<222> LOCATION: (307)..(307)
<223> OTHER INFORMATION: V or K
<220> FEATURE:
<221> NAME/KEY: MISC_FEATURE
<222> LOCATION: (308)..(308)
<223> OTHER INFORMATION: K or E
<220> FEATURE:
<221> NAME/KEY: MISC_FEATURE
<222> LOCATION: (311)..(311)
<223> OTHER INFORMATION: A or K
```

```
<220> FEATURE:
<221> NAME/KEY: MISC_FEATURE
<222> LOCATION: (312)..(312)
<223> OTHER INFORMATION: R or K
<220> FEATURE:
<221> NAME/KEY: MISC_FEATURE
<222> LOCATION: (313)..(313)
<223> OTHER INFORMATION: L or F

<400> SEQUENCE: 1
```

| Met | Xaa | Xaa | Ile | Pro | Leu | Val | Gly | Lys | Xaa | Xaa | Ile | Xaa | Xaa | Xaa | Xaa |
|---|---|---|---|---|---|---|---|---|---|---|---|---|---|---|---|
| 1 | | | | 5 | | | | | 10 | | | | | 15 | |

| Xaa | Gly | Phe | Thr | Leu | Ile | His | Glu | His | Leu | Arg | Val | Phe | Ser | Glu | Xaa |
|---|---|---|---|---|---|---|---|---|---|---|---|---|---|---|---|
| | | | 20 | | | | | 25 | | | | | 30 | | |

| Val | Arg | Tyr | Gln | Trp | Pro | His | Leu | Tyr | Asn | Glu | Asp | Glu | Glu | Xaa | Xaa |
|---|---|---|---|---|---|---|---|---|---|---|---|---|---|---|---|
| | | 35 | | | | | 40 | | | | | 45 | | | |

| Asn | Ala | Val | Asn | Glu | Val | Lys | Xaa | Xaa | Met | Xaa | Xaa | Gly | Val | Lys | Thr |
|---|---|---|---|---|---|---|---|---|---|---|---|---|---|---|---|
| | 50 | | | | | 55 | | | | | 60 | | | | |

| Ile | Val | Asp | Pro | Thr | Val | Met | Gly | Leu | Gly | Arg | Asp | Ile | Arg | Phe | Xaa |
|---|---|---|---|---|---|---|---|---|---|---|---|---|---|---|---|
| 65 | | | | | 70 | | | | | 75 | | | | | 80 |

| Glu | Lys | Val | Val | Lys | Xaa | Thr | Gly | Ile | Asn | Xaa | Xaa | Ala | Xaa | Thr | Gly |
|---|---|---|---|---|---|---|---|---|---|---|---|---|---|---|---|
| | | | | 85 | | | | | 90 | | | | | 95 | |

| Xaa | Tyr | Xaa | Tyr | Xaa | Asp | Leu | Pro | Phe | Xaa | Phe | Xaa | Xaa | Arg | Ser | Xaa |
|---|---|---|---|---|---|---|---|---|---|---|---|---|---|---|---|
| | | | 100 | | | | | 105 | | | | | 110 | | |

| Xaa | Glu | Ile | Ala | Xaa | Leu | Xaa | Ile | His | Asp | Ile | Lys | Xaa | Gly | Ile | Gln |
|---|---|---|---|---|---|---|---|---|---|---|---|---|---|---|---|
| | | 115 | | | | | 120 | | | | | 125 | | | |

| Gly | Thr | Xaa | Asn | Xaa | Ala | Gly | Phe | Xaa | Xaa | Xaa | Ala | Ala | Asp | Glu | Pro |
|---|---|---|---|---|---|---|---|---|---|---|---|---|---|---|---|
| | 130 | | | | | 135 | | | | | 140 | | | | |

| Gly | Ile | Thr | Xaa | Asp | Val | Glu | Xaa | Xaa | Ile | Arg | Ala | Ala | Ile | Ala |
|---|---|---|---|---|---|---|---|---|---|---|---|---|---|---|
| 145 | | | | | 150 | | | | | 155 | | | | 160 |

| Xaa | Lys | Glu | Thr | Xaa | Val | Pro | Ile | Ile | Thr | His | Ser | Asn | Ala | His | Asn |
|---|---|---|---|---|---|---|---|---|---|---|---|---|---|---|---|
| | | | | 165 | | | | | 170 | | | | | 175 | |

| Xaa | Thr | Gly | Leu | Glu | Gln | Gln | Arg | Ile | Leu | Xaa | Glu | Glu | Gly | Val | Asp |
|---|---|---|---|---|---|---|---|---|---|---|---|---|---|---|---|
| | | | 180 | | | | | 185 | | | | | 190 | | |

| Pro | Gly | Xaa | Xaa | Leu | Ile | Gly | His | Leu | Gly | Asp | Thr | Asp | Asn | Xaa | Asp |
|---|---|---|---|---|---|---|---|---|---|---|---|---|---|---|---|
| | | 195 | | | | | 200 | | | | | 205 | | | |

| Tyr | Ile | Lys | Lys | Ile | Ala | Asp | Lys | Gly | Ser | Phe | Xaa | Gly | Leu | Asp | Arg |
|---|---|---|---|---|---|---|---|---|---|---|---|---|---|---|---|
| | 210 | | | | | 215 | | | | | 220 | | | | |

| Tyr | Gly | Leu | Asp | Leu | Phe | Leu | Pro | Xaa | Asp | Lys | Arg | Asn | Glu | Xaa | Xaa |
|---|---|---|---|---|---|---|---|---|---|---|---|---|---|---|---|
| 225 | | | | | 230 | | | | | 235 | | | | | 240 |

| Leu | Xaa | Leu | Ile | Lys | Asp | Gly | Tyr | Xaa | Asp | Xaa | Ile | Met | Xaa | Ser | Xaa |
|---|---|---|---|---|---|---|---|---|---|---|---|---|---|---|---|
| | | | | 245 | | | | | 250 | | | | | 255 | |

| Asp | Tyr | Cys | Cys | Thr | Ile | Asp | Trp | Gly | Xaa | Ala | Lys | Pro | Glu | Tyr | Lys |
|---|---|---|---|---|---|---|---|---|---|---|---|---|---|---|---|
| | | 260 | | | | | 265 | | | | | 270 | | | |

| Pro | Lys | Leu | Ala | Pro | Xaa | Trp | Ser | Xaa | Xaa | Leu | Ile | Phe | Xaa | Asp | Xaa |
|---|---|---|---|---|---|---|---|---|---|---|---|---|---|---|---|
| | 275 | | | | | 280 | | | | | 285 | | | | |

| Ile | Pro | Xaa | Xaa | Lys | Arg | Xaa | Gly | Val | Xaa | Xaa | Glu | Xaa | Xaa | Xaa | Xaa |
|---|---|---|---|---|---|---|---|---|---|---|---|---|---|---|---|
| | | 290 | | | | | 295 | | | | | 300 | | | |

| Ile | Phe | Xaa | Xaa | Asn | Pro | Xaa | Xaa | Xaa | Phe | Ser |
|---|---|---|---|---|---|---|---|---|---|---|
| 305 | | | | 310 | | | | | 315 | |

```
<210> SEQ ID NO 2
<211> LENGTH: 942
<212> TYPE: DNA
<213> ORGANISM: Sulfolobus solfataricus
<220> FEATURE:
<221> NAME/KEY: CDS
<222> LOCATION: (1)..(942)
```

<400> SEQUENCE: 2

```
atg aga ata cca tta gtt ggg aaa gat tca ata gaa tct aag gac ata      48
Met Arg Ile Pro Leu Val Gly Lys Asp Ser Ile Glu Ser Lys Asp Ile
1               5                  10                  15 gga ttt acg cta att cat gaa cat tta aga gtt ttt agc gaa gcg gcc      96
Gly Phe Thr Leu Ile His Glu His Leu Arg Val Phe Ser Glu Ala Ala
            20                  25                  30 aga caa caa tgg ccc cat cta tat aac gaa gat gag gag ttc aga aac     144
Arg Gln Gln Trp Pro His Leu Tyr Asn Glu Asp Glu Glu Phe Arg Asn
        35                  40                  45 gct gta aat gag gtt aaa agg gca atg caa ttt gga gta aag act ata     192
Ala Val Asn Glu Val Lys Arg Ala Met Gln Phe Gly Val Lys Thr Ile
    50                  55                  60 gta gat ccc act gta atg gga ttg ggt agg gac atc aga ttt atg gaa     240
Val Asp Pro Thr Val Met Gly Leu Gly Arg Asp Ile Arg Phe Met Glu
65                  70                  75                  80 aaa gtg gtt aag gct acc ggg ata aat tta gtt gcg ggg acg ggg att     288
Lys Val Val Lys Ala Thr Gly Ile Asn Leu Val Ala Gly Thr Gly Ile
                85                  90                  95 tac ata tat atc gac tta cct ttc tat ttc tta aat agg tca att gat     336
Tyr Ile Tyr Ile Asp Leu Pro Phe Tyr Phe Leu Asn Arg Ser Ile Asp
            100                 105                 110 gag ata gct gac ttg ttt att cat gat ata aaa gag gga ata caa ggt     384
Glu Ile Ala Asp Leu Phe Ile His Asp Ile Lys Glu Gly Ile Gln Gly
        115                 120                 125 act ctc aat aaa gct ggc ttc gta aag ata gct gca gat gaa cct ggg     432
Thr Leu Asn Lys Ala Gly Phe Val Lys Ile Ala Ala Asp Glu Pro Gly
    130                 135                 140 atc aca aag gat gtg gag aag gta ata agg gct gct gcc ata gca aac     480
Ile Thr Lys Asp Val Glu Lys Val Ile Arg Ala Ala Ala Ile Ala Asn
145                 150                 155                 160 aaa gag act aaa gta cca ata att acc cac tct aac gct cac aat aac     528
Lys Glu Thr Lys Val Pro Ile Ile Thr His Ser Asn Ala His Asn Asn
                165                 170                 175 acc gga tta gaa cag caa aga ata ttg act gaa gaa ggt gtt gat cca     576
Thr Gly Leu Glu Gln Gln Arg Ile Leu Thr Glu Glu Gly Val Asp Pro
            180                 185                 190 ggg aaa ata tta ata ggt cat tta ggt gat aca gat aat ata gat tac     624
Gly Lys Ile Leu Ile Gly His Leu Gly Asp Thr Asp Asn Ile Asp Tyr
        195                 200                 205 ata aag aag ata gca gat aag gga tcc ttt att gga tta gat aga tat     672
Ile Lys Lys Ile Ala Asp Lys Gly Ser Phe Ile Gly Leu Asp Arg Tyr
    210                 215                 220 ggt tta gat tta ttc cta cct gtt gat aag aga aat gaa acg acc tta     720
Gly Leu Asp Leu Phe Leu Pro Val Asp Lys Arg Asn Glu Thr Thr Leu
225                 230                 235                 240 aga cta atc aaa gat ggt tat tca gat aag ata atg atc tct cac gat     768
Arg Leu Ile Lys Asp Gly Tyr Ser Asp Lys Ile Met Ile Ser His Asp
                245                 250                 255 tat tgt tgc aca atc gac tgg gga act gca aaa cca gaa tat aaa cct     816
Tyr Cys Cys Thr Ile Asp Trp Gly Thr Ala Lys Pro Glu Tyr Lys Pro
            260                 265                 270 aag ctt gct cca aga tgg agt ata act cta ata ttt gag gat acg ata     864
Lys Leu Ala Pro Arg Trp Ser Ile Thr Leu Ile Phe Glu Asp Thr Ile
        275                 280                 285 ccg ttc tta aag aga aat gga gtg aat gaa gag gtt ata gct aca ata     912
Pro Phe Leu Lys Arg Asn Gly Val Asn Glu Glu Val Ile Ala Thr Ile
    290                 295                 300 ttt aag gaa aat ccg aaa aag ttc ttc agc                             942
Phe Lys Glu Asn Pro Lys Lys Phe Phe Ser
305                 310
```

<210> SEQ ID NO 3
<211> LENGTH: 314
<212> TYPE: PRT
<213> ORGANISM: Sulfolobus solfataricus

<400> SEQUENCE: 3

Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Ala
            20                  25                  30

Arg Gln Gln Trp Pro His Leu Tyr Asn Glu Asp Glu Phe Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Tyr Ile Tyr Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
        115                 120                 125

Thr Leu Asn Lys Ala Gly Phe Val Lys Ile Ala Ala Asp Glu Pro Gly
    130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
        195                 200                 205

Ile Lys Lys Ile Ala Asp Lys Gly Ser Phe Ile Gly Leu Asp Arg Tyr
    210                 215                 220

Gly Leu Asp Leu Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Trp Gly Thr Ala Lys Pro Glu Tyr Lys Pro
            260                 265                 270

Lys Leu Ala Pro Arg Trp Ser Ile Thr Leu Ile Phe Glu Asp Thr Ile
        275                 280                 285

Pro Phe Leu Lys Arg Asn Gly Val Asn Glu Glu Val Ile Ala Thr Ile
    290                 295                 300

Phe Lys Glu Asn Pro Lys Lys Phe Phe Ser
305                 310

<210> SEQ ID NO 4
<211> LENGTH: 945
<212> TYPE: DNA
<213> ORGANISM: Sulfolobus acidocaldarius
<220> FEATURE:
<221> NAME/KEY: CDS
<222> LOCATION: (1)..(945)

<400> SEQUENCE: 4

| | | | | | | | | | | | | | | |
|---|---|---|---|---|---|---|---|---|---|---|---|---|---|---|
| atg | aca | aaa | att | cct | ctt | gta | gga | aaa | ggt | gaa | ata | tca | cct | gga | gaa | 48 |
| Met | Thr | Lys | Ile | Pro | Leu | Val | Gly | Lys | Gly | Glu | Ile | Ser | Pro | Gly | Glu | |
| 1 | | | | 5 | | | | | 10 | | | | | 15 | | |

| atg | ggt | ttt | act | tta | ata | cat | gag | cat | tta | agg | gtc | ttc | agt | gaa | cca | 96 |
| Met | Gly | Phe | Thr | Leu | Ile | His | Glu | His | Leu | Arg | Val | Phe | Ser | Glu | Pro | |
| | | | 20 | | | | | 25 | | | | | 30 | | | |

| gtt | aga | tat | caa | tgg | cca | cat | ctt | tat | aat | gaa | gat | gag | gag | tta | aaa | 144 |
| Val | Arg | Tyr | Gln | Trp | Pro | His | Leu | Tyr | Asn | Glu | Asp | Glu | Glu | Leu | Lys | |
| | | 35 | | | | | 40 | | | | | 45 | | | | |

| aat | gca | gta | aat | gaa | gta | aag | aca | ata | atg | tca | tat | ggt | gtt | aag | acc | 192 |
| Asn | Ala | Val | Asn | Glu | Val | Lys | Thr | Ile | Met | Ser | Tyr | Gly | Val | Lys | Thr | |
| | 50 | | | | | 55 | | | | | 60 | | | | | |

| atc | gtg | gat | ccc | act | gtc | atg | ggt | tta | ggg | aga | gac | att | aga | ttc | agt | 240 |
| Ile | Val | Asp | Pro | Thr | Val | Met | Gly | Leu | Gly | Arg | Asp | Ile | Arg | Phe | Ser | |
| 65 | | | | | 70 | | | | | 75 | | | | | 80 | |

| gag | aag | gtc | gtg | aaa | gaa | aca | ggt | ata | aat | gtg | att | gca | gca | acg | ggg | 288 |
| Glu | Lys | Val | Val | Lys | Glu | Thr | Gly | Ile | Asn | Val | Ile | Ala | Ala | Thr | Gly | |
| | | | | 85 | | | | | 90 | | | | | 95 | | |

| ttg | tat | act | tac | act | gat | tta | cct | ttc | ttc | ttc | aat | gga | aga | tca | ttg | 336 |
| Leu | Tyr | Thr | Tyr | Thr | Asp | Leu | Pro | Phe | Phe | Phe | Asn | Gly | Arg | Ser | Leu | |
| | | | 100 | | | | | 105 | | | | | 110 | | | |

| gaa | gag | att | gca | gaa | tta | tta | ata | cat | gat | ata | aaa | aag | gga | ata | caa | 384 |
| Glu | Glu | Ile | Ala | Glu | Leu | Leu | Ile | His | Asp | Ile | Lys | Lys | Gly | Ile | Gln | |
| | | 115 | | | | | 120 | | | | | 125 | | | | |

| ggg | aca | aat | aat | aga | gca | ggc | ttc | att | aag | gtt | gca | gca | gat | gag | cca | 432 |
| Gly | Thr | Asn | Asn | Arg | Ala | Gly | Phe | Ile | Lys | Val | Ala | Ala | Asp | Glu | Pro | |
| | 130 | | | | | 135 | | | | | 140 | | | | | |

| ggt | ata | acg | agg | gat | gta | gag | agg | gca | ata | agg | gca | gct | gct | ata | gct | 480 |
| Gly | Ile | Thr | Arg | Asp | Val | Glu | Arg | Ala | Ile | Arg | Ala | Ala | Ala | Ile | Ala | |
| 145 | | | | | 150 | | | | | 155 | | | | | 160 | |

| cag | aag | gag | act | aac | gta | ccc | ata | ata | aca | cat | tca | aat | gct | cat | aac | 528 |
| Gln | Lys | Glu | Thr | Asn | Val | Pro | Ile | Ile | Thr | His | Ser | Asn | Ala | His | Asn | |
| | | | | 165 | | | | | 170 | | | | | 175 | | |

| ggg | aca | ggt | ctt | gag | caa | caa | agg | att | cta | atg | gag | gag | ggt | gta | gac | 576 |
| Gly | Thr | Gly | Leu | Glu | Gln | Gln | Arg | Ile | Leu | Met | Glu | Glu | Gly | Val | Asp | |
| | | | 180 | | | | | 185 | | | | | 190 | | | |

| cca | ggg | aga | gtg | cta | ata | ggt | cac | ttg | ggg | gac | act | gat | aac | gtg | gat | 624 |
| Pro | Gly | Arg | Val | Leu | Ile | Gly | His | Leu | Gly | Asp | Thr | Asp | Asn | Val | Asp | |
| | | 195 | | | | | 200 | | | | | 205 | | | | |

| tac | ata | aag | aag | ata | gcc | gat | aaa | ggc | tcg | ttt | gta | ggt | cta | gat | aga | 672 |
| Tyr | Ile | Lys | Lys | Ile | Ala | Asp | Lys | Gly | Ser | Phe | Val | Gly | Leu | Asp | Arg | |
| | 210 | | | | | 215 | | | | | 220 | | | | | |

| tac | ggt | cta | gat | cta | ttc | tta | cct | ata | gat | aaa | agg | aac | gag | gtg | ttg | 720 |
| Tyr | Gly | Leu | Asp | Leu | Phe | Leu | Pro | Ile | Asp | Lys | Arg | Asn | Glu | Val | Leu | |
| 225 | | | | | 230 | | | | | 235 | | | | | 240 | |

| ttg | aaa | tta | att | aaa | gat | gga | tac | ttg | gac | agg | att | atg | gtg | tca | caa | 768 |
| Leu | Lys | Leu | Ile | Lys | Asp | Gly | Tyr | Leu | Asp | Arg | Ile | Met | Val | Ser | Gln | |
| | | | | 245 | | | | | 250 | | | | | 255 | | |

| gat | tac | tgt | tgc | aca | att | gac | tgg | ggg | ata | gca | aag | ccg | gag | tac | aaa | 816 |
| Asp | Tyr | Cys | Cys | Thr | Ile | Asp | Trp | Gly | Ile | Ala | Lys | Pro | Glu | Tyr | Lys | |
| | | | 260 | | | | | 265 | | | | | 270 | | | |

| cct | aaa | cta | gct | cca | aaa | tgg | agt | atg | agt | tta | ata | ttt | aca | gac | gtt | 864 |
| Pro | Lys | Leu | Ala | Pro | Lys | Trp | Ser | Met | Ser | Leu | Ile | Phe | Thr | Asp | Val | |
| | | 275 | | | | | 280 | | | | | 285 | | | | |

| ata | ccc | tca | att | aag | aga | gca | gga | gta | act | gat | gag | cag | ttg | cat | gta | 912 |
| Ile | Pro | Ser | Ile | Lys | Arg | Ala | Gly | Val | Thr | Asp | Glu | Gln | Leu | His | Val | |
| | 290 | | | | | 295 | | | | | 300 | | | | | |

| atc | ttc | gta | aag | aat | cca | gct | aga | cta | ttt | agt | | | | | | 945 |
| Ile | Phe | Val | Lys | Asn | Pro | Ala | Arg | Leu | Phe | Ser | | | | | | |
| 305 | | | | | 310 | | | | | 315 | | | | | | |

<210> SEQ ID NO 5
<211> LENGTH: 315
<212> TYPE: PRT
<213> ORGANISM: Sulfolobus acidocaldarius

<400> SEQUENCE: 5

```
Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
            20                  25                  30

Val Arg Tyr Gln Trp Pro His Leu Tyr Asn Glu Asp Glu Glu Leu Lys
        35                  40                  45

Asn Ala Val Asn Glu Val Lys Thr Ile Met Ser Tyr Gly Val Lys Thr
    50                  55                  60

Ile Val Asp Pro Thr Val Met Gly Leu Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Tyr Thr Tyr Thr Asp Leu Pro Phe Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Asn Asn Arg Ala Gly Phe Ile Lys Val Ala Ala Asp Glu Pro
    130                 135                 140

Gly Ile Thr Arg Asp Val Glu Arg Ala Ile Arg Ala Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp Arg
    210                 215                 220

Tyr Gly Leu Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Cys Cys Thr Ile Asp Trp Gly Ile Ala Lys Pro Glu Tyr Lys
            260                 265                 270

Pro Lys Leu Ala Pro Lys Trp Ser Met Ser Leu Ile Phe Thr Asp Val
        275                 280                 285

Ile Pro Ser Ile Lys Arg Ala Gly Val Thr Asp Glu Gln Leu His Val
    290                 295                 300

Ile Phe Val Lys Asn Pro Ala Arg Leu Phe Ser
305                 310                 315
```

<210> SEQ ID NO 6
<211> LENGTH: 942
<212> TYPE: DNA
<213> ORGANISM: Sulfolobus solfataricus
<220> FEATURE:
<221> NAME/KEY: CDS
<222> LOCATION: (1)..(942)

<400> SEQUENCE: 6

```
atg aga ata cca tta gtt ggg aaa gat tca ata gaa tct aag gac ata    48
Met Arg Ile Pro Leu Val Gly Lys Asp Ser Ile Glu Ser Lys Asp Ile
1               5                   10                  15 gga ttt acg cta att cat gaa cat tta aga gtt ttt agc gaa gcg gcc    96
Gly Phe Thr Leu Ile His Glu His Leu Arg Val Phe Ser Glu Ala Ala
            20                  25                  30 aga caa caa tgg ccc cat cta tat aac gaa gat gag gag ttc aga aac   144
Arg Gln Gln Trp Pro His Leu Tyr Asn Glu Asp Glu Glu Phe Arg Asn
        35                  40                  45 gct gta aat gag gtt aaa agg gca atg caa ttt gga gta aag act ata   192
Ala Val Asn Glu Val Lys Arg Ala Met Gln Phe Gly Val Lys Thr Ile
    50                  55                  60 gta gat ccc act gta atg gga ttg ggt agg gac atc aga ttt atg gaa   240
Val Asp Pro Thr Val Met Gly Leu Gly Arg Asp Ile Arg Phe Met Glu
65                  70                  75                  80 aaa gtg gtt aag gct acc ggg ata aat tta gtt gcg ggg acg ggg att   288
Lys Val Val Lys Ala Thr Gly Ile Asn Leu Val Ala Gly Thr Gly Ile
                85                  90                  95 tgg ata ttc atc gac tta cct ttc tat ttc tta aat agg tca att gat   336
Trp Ile Phe Ile Asp Leu Pro Phe Tyr Phe Leu Asn Arg Ser Ile Asp
            100                 105                 110 gag ata gct gac ttg ttt att cat gat ata aaa gag gga ata caa ggt   384
Glu Ile Ala Asp Leu Phe Ile His Asp Ile Lys Glu Gly Ile Gln Gly
        115                 120                 125 act ctc aat aaa gct ggc ttc gta aag ata gct gca gat gaa cct ggg   432
Thr Leu Asn Lys Ala Gly Phe Val Lys Ile Ala Ala Asp Glu Pro Gly
    130                 135                 140 atc aca aag gat gtg gag aag gta ata agg gct gct gcc ata gca aac   480
Ile Thr Lys Asp Val Glu Lys Val Ile Arg Ala Ala Ala Ile Ala Asn
145                 150                 155                 160 aaa gag act aaa gta cca ata att acc cac tct aac gct cac aat aac   528
Lys Glu Thr Lys Val Pro Ile Ile Thr His Ser Asn Ala His Asn Asn
                165                 170                 175 acc gga tta gaa cag caa aga ata ttg act gaa gaa ggt gtt gat cca   576
Thr Gly Leu Glu Gln Gln Arg Ile Leu Thr Glu Glu Gly Val Asp Pro
            180                 185                 190 ggg aaa ata tta ata ggt cat tta ggt gat aca gat aat ata gat tac   624
Gly Lys Ile Leu Ile Gly His Leu Gly Asp Thr Asp Asn Ile Asp Tyr
        195                 200                 205 ata aag aag ata gca gat aag gga tcc ttt att gga tta gat cat tat   672
Ile Lys Lys Ile Ala Asp Lys Gly Ser Phe Ile Gly Leu Asp His Tyr
    210                 215                 220 ggt tta gat tta ttc cta cct gtt gat aag aga aat gaa acg acc tta   720
Gly Leu Asp Leu Phe Leu Pro Val Asp Lys Arg Asn Glu Thr Thr Leu
225                 230                 235                 240 aga cta atc aaa gat ggt tat tca gat aag ata atg atc tct cac gat   768
Arg Leu Ile Lys Asp Gly Tyr Ser Asp Lys Ile Met Ile Ser His Asp
                245                 250                 255 tat tta tgc aca atc gac tgg gga act gca aaa cca gaa tat aaa cct   816
Tyr Leu Cys Thr Ile Asp Trp Gly Thr Ala Lys Pro Glu Tyr Lys Pro
            260                 265                 270 aag ctt gct cca aga tgg agt ata act cta ata ttt gag gat acg ata   864
Lys Leu Ala Pro Arg Trp Ser Ile Thr Leu Ile Phe Glu Asp Thr Ile
        275                 280                 285 ccg ttc tta aag aga aat gga gtg aat gaa gag gtt ata gct aca ata   912
Pro Phe Leu Lys Arg Asn Gly Val Asn Glu Glu Val Ile Ala Thr Ile
    290                 295                 300 ttt aag gaa aat ccg aaa aag ttc ttc agc                           942
Phe Lys Glu Asn Pro Lys Lys Phe Phe Ser
305                 310
```

<210> SEQ ID NO 7
<211> LENGTH: 314
<212> TYPE: PRT
<213> ORGANISM: Sulfolobus solfataricus

<400> SEQUENCE: 7

Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Ala
            20                  25                  30

Arg Gln Gln Trp Pro His Leu Tyr Asn Glu Asp Glu Glu Phe Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Trp Ile Phe Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
        115                 120                 125

Thr Leu Asn Lys Ala Gly Phe Val Lys Ile Ala Ala Asp Glu Pro Gly
    130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
        195                 200                 205

Ile Lys Lys Ile Ala Asp Lys Gly Ser Phe Ile Gly Leu Asp His Tyr
    210                 215                 220

Gly Leu Asp Leu Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Leu Cys Thr Ile Asp Trp Gly Thr Ala Lys Pro Gly Tyr Lys Pro
            260                 265                 270

Lys Leu Ala Pro Arg Trp Ser Ile Thr Leu Ile Phe Glu Asp Thr Ile
        275                 280                 285

Pro Phe Leu Lys Arg Asn Gly Val Asn Glu Glu Val Ile Ala Thr Ile
    290                 295                 300

Phe Lys Glu Asn Pro Lys Lys Phe Phe Ser
305                 310

<210> SEQ ID NO 8
<211> LENGTH: 942
<212> TYPE: DNA
<213> ORGANISM: Sulfolobus solfataricus
<220> FEATURE:
<221> NAME/KEY: CDS
<222> LOCATION: (1)..(942)

<400> SEQUENCE: 8 atg aga ata cca tta gtt ggg aaa gat tca ata gaa tct aag gac ata    48

```
            Met Arg Ile Pro Leu Val Gly Lys Asp Ser Ile Glu Ser Lys Asp Ile
            1               5                   10                  15 gga ttt acg cta att cat gaa cat tta aga gca ttt agc gaa gcg gcc       96
Gly Phe Thr Leu Ile His Glu His Leu Arg Ala Phe Ser Glu Ala Ala
                20                  25                  30 aga caa caa tgg ccc cat cta tat aac gaa gat gag gag ttc aga aac      144
Arg Gln Gln Trp Pro His Leu Tyr Asn Glu Asp Glu Glu Phe Arg Asn
        35                  40                  45 gct gta aat gag gtt aaa agg gca atg caa ttt gga gta aag act ata      192
Ala Val Asn Glu Val Lys Arg Ala Met Gln Phe Gly Val Lys Thr Ile
    50                  55                  60 gta gat ccc act gta atg gga ata ggt agg gac atc aga ttt atg gaa      240
Val Asp Pro Thr Val Met Gly Ile Gly Arg Asp Ile Arg Phe Met Glu
65                  70                  75                  80 aaa gtg gtt aag gct acc ggg ata aat tta gtt gcg ggg acg ggg att      288
Lys Val Val Lys Ala Thr Gly Ile Asn Leu Val Ala Gly Thr Gly Ile
                85                  90                  95 tgg ata ttc atc gac tta cct ttc tat ttc tta aat agg tca att gat      336
Trp Ile Phe Ile Asp Leu Pro Phe Tyr Phe Leu Asn Arg Ser Ile Asp
                100                 105                 110 gag ata gct gac ttg ttt att cat gat ata aaa gag gga ata caa ggt      384
Glu Ile Ala Asp Leu Phe Ile His Asp Ile Lys Glu Gly Ile Gln Gly
        115                 120                 125 act ctc aat aaa gct ggc ttc gta aag ata gct gca aca gaa cct ggg      432
Thr Leu Asn Lys Ala Gly Phe Val Lys Ile Ala Ala Thr Glu Pro Gly
    130                 135                 140 atc aca aag gat gtg gag aag gta ata agg gct gct gcc ata gca aac      480
Ile Thr Lys Asp Val Glu Lys Val Ile Arg Ala Ala Ala Ile Ala Asn
145                 150                 155                 160 aaa gag act aaa gta cca ata att acc cac tct aac gct cac aat aac      528
Lys Glu Thr Lys Val Pro Ile Ile Thr His Ser Asn Ala His Asn Asn
                165                 170                 175 acc gga tta gaa cag caa aga ata ttg act gaa gaa ggt gtt gat cca      576
Thr Gly Leu Glu Gln Gln Arg Ile Leu Thr Glu Glu Gly Val Asp Pro
                180                 185                 190 ggg aaa ata tta ata ggt cat tta ggt gat aca gat aat ata gat tac      624
Gly Lys Ile Leu Ile Gly His Leu Gly Asp Thr Asp Asn Ile Asp Tyr
        195                 200                 205 ata aag aag ata gca gat aag gga tcc ttt att gga tta gat cat tat      672
Ile Lys Lys Ile Ala Asp Lys Gly Ser Phe Ile Gly Leu Asp His Tyr
    210                 215                 220 ccg cat gat tta ttc cta cct gtt gat aag aga aat gaa acg acc tta      720
Pro His Asp Leu Phe Leu Pro Val Asp Lys Arg Asn Glu Thr Thr Leu
225                 230                 235                 240 aga cta atc aaa gat ggt tat tca gat aag ata atg atc tct cac gat      768
Arg Leu Ile Lys Asp Gly Tyr Ser Asp Lys Ile Met Ile Ser His Asp
                245                 250                 255 tat tta tgc aca atc gac tgg gga act gca aaa cca gaa tat aaa cct      816
Tyr Leu Cys Thr Ile Asp Trp Gly Thr Ala Lys Pro Glu Tyr Lys Pro
                260                 265                 270 aag ctt gct cca aga tgg agt ata act cta ata ttt gag gat acg ata      864
Lys Leu Ala Pro Arg Trp Ser Ile Thr Leu Ile Phe Glu Asp Thr Ile
        275                 280                 285 ccg ttc tta aag aga aat gga gtg aat gaa gag gtt ata gct aca ata      912
Pro Phe Leu Lys Arg Asn Gly Val Asn Glu Glu Val Ile Ala Thr Ile
    290                 295                 300 ttt aag gaa aat ccg aaa aag ttc ttc agc                              942
Phe Lys Glu Asn Pro Lys Lys Phe Phe Ser
305                 310
```

<210> SEQ ID NO 9
<211> LENGTH: 314
<212> TYPE: PRT
<213> ORGANISM: Sulfolobus solfataricus

<400> SEQUENCE: 9

Met Arg Ile Pro Leu Val Gly Lys Asp Ser Ile Glu Ser Lys Asp Ile
1               5                   10                  15

Gly Phe Thr Leu Ile His Glu His Leu Arg Ala Phe Ser Glu Ala Ala
            20                  25                  30

Arg Gln Gln Trp Pro His Leu Tyr Asn Glu Asp Glu Phe Arg Asn
        35                  40                  45

Ala Val Asn Glu Val Lys Arg Ala Met Gln Phe Gly Val Lys Thr Ile
    50                  55                  60

Val Asp Pro Thr Val Met Gly Ile Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Trp Ile Phe Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
        115                 120                 125

Thr Leu Asn Lys Ala Gly Phe Val Lys Ile Ala Ala Thr Glu Pro Gly
130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
        195                 200                 205

Ile Lys Lys Ile Ala Asp Lys Gly Ser Phe Ile Gly Leu Asp His Tyr
    210                 215                 220

Pro His Asp Leu Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Leu Cys Thr Ile Asp Trp Gly Thr Ala Lys Pro Glu Tyr Lys Pro
            260                 265                 270

Lys Leu Ala Pro Arg Trp Ser Ile Thr Leu Ile Phe Glu Asp Thr Ile
        275                 280                 285

Pro Phe Leu Lys Arg Asn Gly Val Asn Glu Glu Val Ile Ala Thr Ile
    290                 295                 300

Phe Lys Glu Asn Pro Lys Lys Phe Phe Ser
305                 310

<210> SEQ ID NO 10
<211> LENGTH: 942
<212> TYPE: DNA
<213> ORGANISM: Sulfolobus solfataricus
<220> FEATURE:
<221> NAME/KEY: CDS
<222> LOCATION: (1)..(942)

<400> SEQUENCE: 10 atg aga ata cca tta gtt ggg aaa gat tca ata gaa tct aag gac ata      48
Met Arg Ile Pro Leu Val Gly Lys Asp Ser Ile Glu Ser Lys Asp Ile

|   |   |   |   |   |   |   |   |   |   |   |   |   |   |   |   |   |
|---|---|---|---|---|---|---|---|---|---|---|---|---|---|---|---|---|
| 1 |   |   |   | 5 |   |   |   |   | 10 |   |   |   |   | 15 |   |   |
| gga | ttt | acg | cta | att | cat | gaa | cat | tta | aga | gca | ttt | agc | gaa | gcg | gcc | 96 |
| Gly | Phe | Thr | Leu | Ile | His | Glu | His | Leu | Arg | Ala | Phe | Ser | Glu | Ala | Ala |   |
|   |   |   | 20 |   |   |   |   | 25 |   |   |   |   | 30 |   |   |   |
| aga | caa | caa | tgg | ccc | cat | cta | tat | aac | gaa | gat | gag | gag | ttc | aga | aac | 144 |
| Arg | Gln | Gln | Trp | Pro | His | Leu | Tyr | Asn | Glu | Asp | Glu | Glu | Phe | Arg | Asn |   |
|   |   | 35 |   |   |   |   | 40 |   |   |   |   | 45 |   |   |   |   |
| gct | gta | aat | gag | gtt | aaa | agg | gca | atg | caa | ttt | gga | gta | aag | act | ata | 192 |
| Ala | Val | Asn | Glu | Val | Lys | Arg | Ala | Met | Gln | Phe | Gly | Val | Lys | Thr | Ile |   |
|   | 50 |   |   |   |   | 55 |   |   |   |   | 60 |   |   |   |   |   |
| gta | gat | gtt | agc | gta | atg | gga | ata | ggt | agg | gac | atc | aga | ttt | atg | gaa | 240 |
| Val | Asp | Val | Ser | Val | Met | Gly | Ile | Gly | Arg | Asp | Ile | Arg | Phe | Met | Glu |   |
| 65 |   |   |   |   | 70 |   |   |   |   | 75 |   |   |   |   | 80 |   |
| aaa | gtg | gtt | aag | gct | acc | ggg | ata | aat | tta | gtt | gcg | ggg | acg | ggg | att | 288 |
| Lys | Val | Val | Lys | Ala | Thr | Gly | Ile | Asn | Leu | Val | Ala | Gly | Thr | Gly | Ile |   |
|   |   |   |   | 85 |   |   |   |   | 90 |   |   |   |   | 95 |   |   |
| tgg | ata | ttc | atc | gac | tta | cct | ttc | tat | ttc | tta | aat | agg | tca | att | gat | 336 |
| Trp | Ile | Phe | Ile | Asp | Leu | Pro | Phe | Tyr | Phe | Leu | Asn | Arg | Ser | Ile | Asp |   |
|   |   |   | 100 |   |   |   |   | 105 |   |   |   |   | 110 |   |   |   |
| gag | ata | gct | gac | ttg | ttt | att | cat | gat | ata | aaa | gag | gga | ata | caa | ggt | 384 |
| Glu | Ile | Ala | Asp | Leu | Phe | Ile | His | Asp | Ile | Lys | Glu | Gly | Ile | Gln | Gly |   |
|   |   | 115 |   |   |   |   | 120 |   |   |   |   | 125 |   |   |   |   |
| act | ctc | aat | aaa | gct | ggc | ttc | gta | aag | ata | gct | gca | aca | gaa | cct | ggg | 432 |
| Thr | Leu | Asn | Lys | Ala | Gly | Phe | Val | Lys | Ile | Ala | Ala | Thr | Glu | Pro | Gly |   |
|   | 130 |   |   |   |   | 135 |   |   |   |   | 140 |   |   |   |   |   |
| atc | aca | aag | gat | gtg | gag | aag | gta | ata | agg | gct | gct | gcc | ata | gca | aac | 480 |
| Ile | Thr | Lys | Asp | Val | Glu | Lys | Val | Ile | Arg | Ala | Ala | Ala | Ile | Ala | Asn |   |
| 145 |   |   |   |   | 150 |   |   |   |   | 155 |   |   |   |   | 160 |   |
| aaa | gag | act | aaa | gta | cca | ata | att | acc | cac | tct | aac | gct | cac | aat | aac | 528 |
| Lys | Glu | Thr | Lys | Val | Pro | Ile | Ile | Thr | His | Ser | Asn | Ala | His | Asn | Asn |   |
|   |   |   |   | 165 |   |   |   |   | 170 |   |   |   |   | 175 |   |   |
| acc | gga | tta | gaa | cag | caa | aga | ata | ttg | act | gaa | gaa | ggt | gtt | gat | cca | 576 |
| Thr | Gly | Leu | Glu | Gln | Gln | Arg | Ile | Leu | Thr | Glu | Glu | Gly | Val | Asp | Pro |   |
|   |   |   | 180 |   |   |   |   | 185 |   |   |   |   | 190 |   |   |   |
| ggg | aaa | ata | tta | ata | ggt | cat | tta | ggt | gat | aca | gat | aat | ata | gat | tac | 624 |
| Gly | Lys | Ile | Leu | Ile | Gly | His | Leu | Gly | Asp | Thr | Asp | Asn | Ile | Asp | Tyr |   |
|   |   | 195 |   |   |   |   | 200 |   |   |   |   | 205 |   |   |   |   |
| ata | aag | aag | ata | gca | gat | aag | gga | tcc | ttt | att | gga | tta | gat | cat | tat | 672 |
| Ile | Lys | Lys | Ile | Ala | Asp | Lys | Gly | Ser | Phe | Ile | Gly | Leu | Asp | His | Tyr |   |
|   | 210 |   |   |   |   | 215 |   |   |   |   | 220 |   |   |   |   |   |
| ccg | cat | gat | tta | tca | cta | cct | gtt | gat | aag | aga | aat | gaa | acg | acc | tta | 720 |
| Pro | His | Asp | Leu | Ser | Leu | Pro | Val | Asp | Lys | Arg | Asn | Glu | Thr | Thr | Leu |   |
| 225 |   |   |   |   | 230 |   |   |   |   | 235 |   |   |   |   | 240 |   |
| aga | cta | atc | aaa | gat | ggt | tat | tca | gat | aag | ata | atg | atc | tct | cac | gat | 768 |
| Arg | Leu | Ile | Lys | Asp | Gly | Tyr | Ser | Asp | Lys | Ile | Met | Ile | Ser | His | Asp |   |
|   |   |   |   | 245 |   |   |   |   | 250 |   |   |   |   | 255 |   |   |
| tat | tta | tgc | aca | atc | gac | gca | gga | act | gca | aaa | cca | gaa | tat | aaa | cct | 816 |
| Tyr | Leu | Cys | Thr | Ile | Asp | Ala | Gly | Thr | Ala | Lys | Pro | Glu | Tyr | Lys | Pro |   |
|   |   |   | 260 |   |   |   |   | 265 |   |   |   |   | 270 |   |   |   |
| aag | ctt | gct | cca | aga | atc | agt | ata | act | cta | ata | ttt | gag | gat | acg | ata | 864 |
| Lys | Leu | Ala | Pro | Arg | Ile | Ser | Ile | Thr | Leu | Ile | Phe | Glu | Asp | Thr | Ile |   |
|   |   | 275 |   |   |   |   | 280 |   |   |   |   | 285 |   |   |   |   |
| ccg | ttc | tta | aag | aga | aat | gga | gtg | aat | gaa | gag | gtt | ata | gct | aca | ata | 912 |
| Pro | Phe | Leu | Lys | Arg | Asn | Gly | Val | Asn | Glu | Glu | Val | Ile | Ala | Thr | Ile |   |
|   | 290 |   |   |   |   | 295 |   |   |   |   | 300 |   |   |   |   |   |
| ttt | aag | gaa | aat | ccg | aaa | aag | ttc | ttc | agc |   |   |   |   |   |   | 942 |
| Phe | Lys | Glu | Asn | Pro | Lys | Lys | Phe | Phe | Ser |   |   |   |   |   |   |   |
| 305 |   |   |   |   | 310 |   |   |   |   |   |   |   |   |   |   |   |

<210> SEQ ID NO 11

<211> LENGTH: 314
<212> TYPE: PRT
<213> ORGANISM: Sulfolobus solfataricus

<400> SEQUENCE: 11

```
Met Arg Ile Pro Leu Val Gly Lys Asp Ser Ile Glu Ser Lys Asp Ile
1               5                   10                  15

Gly Phe Thr Leu Ile His Glu His Leu Arg Ala Phe Ser Glu Ala Ala
            20                  25                  30

Arg Gln Gln Trp Pro His Leu Tyr Asn Glu Asp Glu Phe Arg Asn
        35                  40                  45

Ala Val Asn Glu Val Lys Arg Ala Met Gln Phe Gly Val Lys Thr Ile
    50                  55                  60

Val Asp Val Ser Val Met Gly Ile Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Trp Ile Phe Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
        115                 120                 125

Thr Leu Asn Lys Ala Gly Phe Val Lys Ile Ala Ala Thr Glu Pro Gly
130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
        195                 200                 205

Ile Lys Lys Ile Ala Asp Lys Gly Ser Phe Ile Gly Leu Asp His Tyr
    210                 215                 220

Pro His Asp Leu Ser Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Leu Cys Thr Ile Asp Ala Gly Thr Ala Lys Pro Glu Tyr Lys Pro
            260                 265                 270

Lys Leu Ala Pro Arg Ile Ser Ile Thr Leu Ile Phe Glu Asp Thr Ile
        275                 280                 285

Pro Phe Leu Lys Arg Asn Gly Val Asn Glu Glu Val Ile Ala Thr Ile
    290                 295                 300

Phe Lys Glu Asn Pro Lys Lys Phe Phe Ser
305                 310
```

<210> SEQ ID NO 12
<211> LENGTH: 945
<212> TYPE: DNA
<213> ORGANISM: Sulfolobus acidocaldarius
<220> FEATURE:
<221> NAME/KEY: CDS
<222> LOCATION: (1)..(945)

<400> SEQUENCE: 12

```
atg aca aaa att cct ctt gta gga aaa ggt gaa ata tca cct gga gaa    48
Met Thr Lys Ile Pro Leu Val Gly Lys Gly Glu Ile Ser Pro Gly Glu
1               5                   10                  15
```

```
atg ggt ttt act tta ata cat gag cat tta agg gtc ttc agt gaa cca      96
Met Gly Phe Thr Leu Ile His Glu His Leu Arg Val Phe Ser Glu Pro
         20                  25                  30 gtt aga tat caa tgg cca cat ctt tat aat gaa gat gag gag tta aaa     144
Val Arg Tyr Gln Trp Pro His Leu Tyr Asn Glu Asp Glu Glu Leu Lys
     35                  40                  45 aat gca gta aat gaa gta aag aca ata atg tca tat ggt gtt aag acc     192
Asn Ala Val Asn Glu Val Lys Thr Ile Met Ser Tyr Gly Val Lys Thr
 50                  55                  60 atc gtg gat ccc act gtc atg ggt tta ggg aga gac att aga ttc agt     240
Ile Val Asp Pro Thr Val Met Gly Leu Gly Arg Asp Ile Arg Phe Ser
 65                  70                  75                  80 gag aag gtc gtg aaa gaa aca ggt ata aat gtg att gca gca acg ggg     288
Glu Lys Val Val Lys Glu Thr Gly Ile Asn Val Ile Ala Ala Thr Gly
                 85                  90                  95 ttg tgg act ttt act gat tta cct ttc ttc ttc aat gga aga tca ttg     336
Leu Trp Thr Phe Thr Asp Leu Pro Phe Phe Phe Asn Gly Arg Ser Leu
            100                 105                 110 gaa gag att gca gaa tta tta ata cat gat ata aaa aag gga ata caa     384
Glu Glu Ile Ala Glu Leu Leu Ile His Asp Ile Lys Lys Gly Ile Gln
        115                 120                 125 ggg aca aat aat aga gca ggc ttc att aag gtt gca gca gat gag cca     432
Gly Thr Asn Asn Arg Ala Gly Phe Ile Lys Val Ala Ala Asp Glu Pro
130                 135                 140 ggt ata acg agg gat gta gag agg gca ata agg gca gct gct ata gct     480
Gly Ile Thr Arg Asp Val Glu Arg Ala Ile Arg Ala Ala Ala Ile Ala
145                 150                 155                 160 cag aag gag act aac gta ccc ata ata aca cat tca aat gct cat aac     528
Gln Lys Glu Thr Asn Val Pro Ile Ile Thr His Ser Asn Ala His Asn
                165                 170                 175 ggg aca ggt ctt gag caa caa agg att cta atg gag gag ggt gta gac     576
Gly Thr Gly Leu Glu Gln Gln Arg Ile Leu Met Glu Glu Gly Val Asp
            180                 185                 190 cca ggg aga gtg cta ata ggt cac ttg ggg gac act gat aac gtg gat     624
Pro Gly Arg Val Leu Ile Gly His Leu Gly Asp Thr Asp Asn Val Asp
        195                 200                 205 tac ata aag aag ata gcc gat aaa ggc tcg ttt gta ggt cta gat cat     672
Tyr Ile Lys Lys Ile Ala Asp Lys Gly Ser Phe Val Gly Leu Asp His
    210                 215                 220 tac ggt cta gat cta ttc tta cct ata gat aaa agg aac gag gtg ttg     720
Tyr Gly Leu Asp Leu Phe Leu Pro Ile Asp Lys Arg Asn Glu Val Leu
225                 230                 235                 240 ttg aaa tta att aaa gat gga tac ttg gac agg att atg gtg tca caa     768
Leu Lys Leu Ile Lys Asp Gly Tyr Leu Asp Arg Ile Met Val Ser Gln
                245                 250                 255 gat tac tta tgc aca att gac tgg ggg ata gca aag ccg gag tac aaa     816
Asp Tyr Leu Cys Thr Ile Asp Trp Gly Ile Ala Lys Pro Glu Tyr Lys
            260                 265                 270 cct aaa cta gct cca aaa tgg agt atg agt tta ata ttt aca gac gtt     864
Pro Lys Leu Ala Pro Lys Trp Ser Met Ser Leu Ile Phe Thr Asp Val
        275                 280                 285 ata ccc tca att aag aga gca gga gta act gat gag cag ttg cat gta     912
Ile Pro Ser Ile Lys Arg Ala Gly Val Thr Asp Glu Gln Leu His Val
    290                 295                 300 atc ttc gta aag aat cca gct aga cta ttt agt                         945
Ile Phe Val Lys Asn Pro Ala Arg Leu Phe Ser
305                 310                 315

<210> SEQ ID NO 13
<211> LENGTH: 315
```

<212> TYPE: PRT
<213> ORGANISM: Sulfolobus acidocaldarius

<400> SEQUENCE: 13

Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
            20                  25                  30

Val Arg Tyr Gln Trp Pro His Leu Tyr Asn Glu Asp Glu Glu Leu Lys
        35                  40                  45

Asn Ala Val Asn Glu Val Lys Thr Ile Met Ser Tyr Gly Val Lys Thr
    50                  55                  60

Ile Val Asp Pro Thr Val Met Gly Leu Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Trp Thr Phe Thr Asp Leu Pro Phe Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Asn Asn Arg Ala Gly Phe Ile Lys Val Ala Ala Asp Glu Pro
    130                 135                 140

Gly Ile Thr Arg Asp Val Glu Arg Ala Ile Ala Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp His
    210                 215                 220

Tyr Gly Leu Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Leu Cys Thr Ile Asp Trp Gly Ile Ala Lys Pro Glu Tyr Lys
            260                 265                 270

Pro Lys Leu Ala Pro Lys Trp Ser Met Ser Leu Ile Phe Thr Asp Val
        275                 280                 285

Ile Pro Ser Ile Lys Arg Ala Gly Val Thr Asp Glu Gln Leu His Val
    290                 295                 300

Ile Phe Val Lys Asn Pro Ala Arg Leu Phe Ser
305                 310                 315

<210> SEQ ID NO 14
<211> LENGTH: 945
<212> TYPE: DNA
<213> ORGANISM: Sulfolobus acidocaldarius
<220> FEATURE:
<221> NAME/KEY: CDS
<222> LOCATION: (1)..(945)

<400> SEQUENCE: 14 atg aca aaa att cct ctt gta gga aaa ggt gaa ata tca cct gga gaa    48
Met Thr Lys Ile Pro Leu Val Gly Lys Gly Glu Ile Ser Pro Gly Glu
1               5                   10                  15

```
atg ggt ttt act tta ata cat gag cat tta agg gca ttc agt gaa cca    96
Met Gly Phe Thr Leu Ile His Glu His Leu Arg Ala Phe Ser Glu Pro
         20                  25                  30 gtt aga tat caa tgg cca cat ctt tat aat gaa gat gag gag tta aaa   144
Val Arg Tyr Gln Trp Pro His Leu Tyr Asn Glu Asp Glu Glu Leu Lys
     35                  40                  45 aat gca gta aat gaa gta aag aca ata atg tca tat ggt gtt aag acc   192
Asn Ala Val Asn Glu Val Lys Thr Ile Met Ser Tyr Gly Val Lys Thr
 50                  55                  60 atc gtg gat ccc act gtc atg ggt atc ggg aga gac att aga ttc agt   240
Ile Val Asp Pro Thr Val Met Gly Ile Gly Arg Asp Ile Arg Phe Ser
 65                  70                  75                  80 gag aag gtc gtg aaa gaa aca ggt ata aat gtg att gca gca acg ggg   288
Glu Lys Val Val Lys Glu Thr Gly Ile Asn Val Ile Ala Ala Thr Gly
                 85                  90                  95 ttg tgg act ttt act gat tta cct ttc ttc ttc aat gga aga tca ttg   336
Leu Trp Thr Phe Thr Asp Leu Pro Phe Phe Phe Asn Gly Arg Ser Leu
            100                 105                 110 gaa gag att gca gaa tta tta ata cat gat ata aaa aag gga ata caa   384
Glu Glu Ile Ala Glu Leu Leu Ile His Asp Ile Lys Lys Gly Ile Gln
        115                 120                 125 ggg aca aat aat aga gca ggc ttc att aag gtt gca gca aca gag cca   432
Gly Thr Asn Asn Arg Ala Gly Phe Ile Lys Val Ala Ala Thr Glu Pro
    130                 135                 140 ggt ata acg agg gat gta gag agg gca ata agg gca gct gct ata gct   480
Gly Ile Thr Arg Asp Val Glu Arg Ala Ile Arg Ala Ala Ala Ile Ala
145                 150                 155                 160 cag aag gag act aac gta ccc ata ata aca cat tca aat gct cat aac   528
Gln Lys Glu Thr Asn Val Pro Ile Ile Thr His Ser Asn Ala His Asn
                165                 170                 175 ggg aca ggt ctt gag caa caa agg att cta atg gag gag ggt gta gac   576
Gly Thr Gly Leu Glu Gln Gln Arg Ile Leu Met Glu Glu Gly Val Asp
            180                 185                 190 cca ggg aga gtg cta ata ggt cac ttg ggg gac act gat aac gtg gat   624
Pro Gly Arg Val Leu Ile Gly His Leu Gly Asp Thr Asp Asn Val Asp
        195                 200                 205 tac ata aag aag ata gcc gat aaa ggc tcg ttt gta ggt cta gat cat   672
Tyr Ile Lys Lys Ile Ala Asp Lys Gly Ser Phe Val Gly Leu Asp His
    210                 215                 220 tac cca cat gat cta ttc tta cct ata gat aaa agg aac gag gtg ttg   720
Tyr Pro His Asp Leu Phe Leu Pro Ile Asp Lys Arg Asn Glu Val Leu
225                 230                 235                 240 ttg aaa tta att aaa gat gga tac ttg gac agg att atg gtg tca caa   768
Leu Lys Leu Ile Lys Asp Gly Tyr Leu Asp Arg Ile Met Val Ser Gln
                245                 250                 255 gat tac tta tgc aca att gac tgg ggg ata gca aag ccg gag tac aaa   816
Asp Tyr Leu Cys Thr Ile Asp Trp Gly Ile Ala Lys Pro Glu Tyr Lys
            260                 265                 270 cct aaa cta gct cca aaa tgg agt atg agt tta ata ttt aca gac gtt   864
Pro Lys Leu Ala Pro Lys Trp Ser Met Ser Leu Ile Phe Thr Asp Val
        275                 280                 285 ata ccc tca att aag aga gca gga gta act gat gag cag ttg cat gta   912
Ile Pro Ser Ile Lys Arg Ala Gly Val Thr Asp Glu Gln Leu His Val
    290                 295                 300 atc ttc gta aag aat cca gct aga cta ttt agt                       945
Ile Phe Val Lys Asn Pro Ala Arg Leu Phe Ser
305                 310                 315

<210> SEQ ID NO 15
<211> LENGTH: 315
<212> TYPE: PRT
```

<213> ORGANISM: Sulfolobus acidocaldarius

<400> SEQUENCE: 15

Met Thr Lys Ile Pro Leu Val Gly Lys Gly Glu Ile Ser Pro Gly Glu
1               5                   10                  15

Met Gly Phe Thr Leu Ile His Glu His Leu Arg Ala Phe Ser Glu Pro
            20                  25                  30

Val Arg Tyr Gln Trp Pro His Leu Tyr Asn Glu Asp Glu Leu Lys
        35                  40                  45

Asn Ala Val Asn Glu Val Lys Thr Ile Met Ser Tyr Gly Val Lys Thr
    50                  55                  60

Ile Val Asp Pro Thr Val Met Gly Ile Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Trp Thr Phe Thr Asp Leu Pro Phe Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Asn Asn Arg Ala Gly Phe Ile Lys Val Ala Ala Thr Glu Pro
    130                 135                 140

Gly Ile Thr Arg Asp Val Glu Arg Ala Ile Arg Ala Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp His
    210                 215                 220

Tyr Pro His Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Leu Cys Thr Ile Asp Trp Gly Ile Ala Lys Pro Glu Tyr Lys
            260                 265                 270

Pro Lys Leu Ala Pro Lys Trp Ser Met Ser Leu Ile Phe Thr Asp Val
        275                 280                 285

Ile Pro Ser Ile Lys Arg Ala Gly Val Thr Asp Glu Gln Leu His Val
    290                 295                 300

Ile Phe Val Lys Asn Pro Ala Arg Leu Phe Ser
305                 310                 315

<210> SEQ ID NO 16
<211> LENGTH: 945
<212> TYPE: DNA
<213> ORGANISM: Sulfolobus acidocaldarius
<220> FEATURE:
<221> NAME/KEY: CDS
<222> LOCATION: (1)..(945)

<400> SEQUENCE: 16 atg aca aaa att cct ctt gta gga aaa ggt gaa ata tca cct gga gaa    48
Met Thr Lys Ile Pro Leu Val Gly Lys Gly Glu Ile Ser Pro Gly Glu
1               5                   10                  15 atg ggt ttt act tta ata cat gag cat tta agg gca ttc agt gaa cca    96

```
            Met Gly Phe Thr Leu Ile His Glu His Leu Arg Ala Phe Ser Glu Pro
                         20                  25                  30 gtt aga tat caa tgg cca cat ctt tat aat gaa gat gag gag tta aaa         144
Val Arg Tyr Gln Trp Pro His Leu Tyr Asn Glu Asp Glu Glu Leu Lys
             35                  40                  45 aat gca gta aat gaa gta aag aca ata atg tca tat ggt gtt aag acc         192
Asn Ala Val Asn Glu Val Lys Thr Ile Met Ser Tyr Gly Val Lys Thr
 50                  55                  60 atc gtg gat gta tca gtc atg ggt atc ggg aga gac att aga ttc agt         240
Ile Val Asp Val Ser Val Met Gly Ile Gly Arg Asp Ile Arg Phe Ser
 65                  70                  75                  80 gag aag gtc gtg aaa gaa aca ggt ata aat gtg att gca gca acg ggg         288
Glu Lys Val Val Lys Glu Thr Gly Ile Asn Val Ile Ala Ala Thr Gly
                 85                  90                  95 ttg tgg act ttt act gat tta cct ttc ttc ttc aat gga aga tca ttg         336
Leu Trp Thr Phe Thr Asp Leu Pro Phe Phe Phe Asn Gly Arg Ser Leu
            100                 105                 110 gaa gag att gca gaa tta tta ata cat gat ata aaa aag gga ata caa         384
Glu Glu Ile Ala Glu Leu Leu Ile His Asp Ile Lys Lys Gly Ile Gln
        115                 120                 125 ggg aca aat aat aga gca ggc ttc att aag gtt gca gca aca gag cca         432
Gly Thr Asn Asn Arg Ala Gly Phe Ile Lys Val Ala Ala Thr Glu Pro
    130                 135                 140 ggt ata acg agg gat gta gag agg gca ata agg gca gct gct ata gct         480
Gly Ile Thr Arg Asp Val Glu Arg Ala Ile Arg Ala Ala Ala Ile Ala
145                 150                 155                 160 cag aag gag act aac gta ccc ata ata aca cat tca aat gct cat aac         528
Gln Lys Glu Thr Asn Val Pro Ile Ile Thr His Ser Asn Ala His Asn
                165                 170                 175 ggg aca ggt ctt gag caa caa agg att cta atg gag gag ggt gta gac         576
Gly Thr Gly Leu Glu Gln Gln Arg Ile Leu Met Glu Glu Gly Val Asp
            180                 185                 190 cca ggg aga gtg cta ata ggt cac ttg ggg gac act gat aac gtg gat         624
Pro Gly Arg Val Leu Ile Gly His Leu Gly Asp Thr Asp Asn Val Asp
        195                 200                 205 tac ata aag aag ata gcc gat aaa ggc tcg ttt gta ggt cta gat cat         672
Tyr Ile Lys Lys Ile Ala Asp Lys Gly Ser Phe Val Gly Leu Asp His
    210                 215                 220 tac cca cat gat cta tca tta cct ata gat aaa agg aac gag gtg ttg         720
Tyr Pro His Asp Leu Ser Leu Pro Ile Asp Lys Arg Asn Glu Val Leu
225                 230                 235                 240 ttg aaa tta att aaa gat gga tac ttg gac agg att atg gtg tca caa         768
Leu Lys Leu Ile Lys Asp Gly Tyr Leu Asp Arg Ile Met Val Ser Gln
                245                 250                 255 gat tac tta tgc aca att gac gca ggg ata gca aag ccg gag tac aaa         816
Asp Tyr Leu Cys Thr Ile Asp Ala Gly Ile Ala Lys Pro Glu Tyr Lys
            260                 265                 270 cct aaa cta gct cca aaa att agt atg agt tta ata ttt aca gac gtt         864
Pro Lys Leu Ala Pro Lys Ile Ser Met Ser Leu Ile Phe Thr Asp Val
        275                 280                 285 ata ccc tca att aag aga gca gga gta act gat gag cag ttg cat gta         912
Ile Pro Ser Ile Lys Arg Ala Gly Val Thr Asp Glu Gln Leu His Val
    290                 295                 300 atc ttc gta aag aat cca gct aga cta ttt agt                             945
Ile Phe Val Lys Asn Pro Ala Arg Leu Phe Ser
305                 310                 315

<210> SEQ ID NO 17
<211> LENGTH: 315
<212> TYPE: PRT
<213> ORGANISM: Sulfolobus acidocaldarius
```

<400> SEQUENCE: 17

```
Met Thr Lys Ile Pro Leu Val Gly Lys Gly Glu Ile Ser Pro Gly Glu
1               5                   10                  15

Met Gly Phe Thr Leu Ile His Glu His Leu Arg Ala Phe Ser Glu Pro
            20                  25                  30

Val Arg Tyr Gln Trp Pro His Leu Tyr Asn Glu Asp Glu Glu Leu Lys
        35                  40                  45

Asn Ala Val Asn Glu Val Lys Thr Ile Met Ser Tyr Gly Val Lys Thr
    50                  55                  60

Ile Val Asp Val Ser Val Met Gly Ile Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Trp Thr Phe Thr Asp Leu Pro Phe Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Asn Asn Arg Ala Gly Phe Ile Lys Val Ala Ala Thr Glu Pro
    130                 135                 140

Gly Ile Thr Arg Asp Val Glu Arg Ala Ile Arg Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp His
210                 215                 220

Tyr Pro His Asp Leu Ser Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Leu Cys Thr Ile Asp Ala Gly Ile Ala Lys Pro Glu Tyr Lys
            260                 265                 270

Pro Lys Leu Ala Pro Lys Ile Ser Met Ser Leu Ile Phe Thr Asp Val
        275                 280                 285

Ile Pro Ser Ile Lys Arg Ala Gly Val Thr Asp Glu Gln Leu His Val
290                 295                 300

Ile Phe Val Lys Asn Pro Ala Arg Leu Phe Ser
305                 310                 315
```

<210> SEQ ID NO 18
<211> LENGTH: 102
<212> TYPE: DNA
<213> ORGANISM: Sulfolobus solfataricus

<400> SEQUENCE: 18

```
gatatacata tgagaatacc attagttggg aaagattcaa tagaatctaa ggacatagga      60
tttacgctaa ttcatgaaca tttaagagct tttagcgaag cg                        102
```

<210> SEQ ID NO 19
<211> LENGTH: 92
<212> TYPE: DNA
<213> ORGANISM: Sulfolobus solfataricus

```
<400> SEQUENCE: 19
aacctcattt acagcgtttc tgaactcctc atcttcgtta tatagatggg ccattgttgt      60
ctgaccgctt cgctaaaagc tcttaaatgt tc                                   92

<210> SEQ ID NO 20
<211> LENGTH: 93
<212> TYPE: DNA
<213> ORGANISM: Sulfolobus solfataricus

<400> SEQUENCE: 20
gagttcagaa acgctgtaaa tgaggttaaa agggcaatgc aatttggagt aaagactata      60
gtagatgtct ctgtaatggg aattggtagg gac                                  93

<210> SEQ ID NO 21
<211> LENGTH: 93
<212> TYPE: DNA
<213> ORGANISM: Sulfolobus solfataricus

<400> SEQUENCE: 21
cgtccccgca actaaattta tcccggtagc cttaaccact ttttccataa atctgatgtc      60
cctaccaatt cccattacag agacatctac tat                                  93

<210> SEQ ID NO 22
<211> LENGTH: 93
<212> TYPE: DNA
<213> ORGANISM: Sulfolobus solfataricus

<400> SEQUENCE: 22
accgggataa atttagttgc ggggacgggg atttggatat ttatcgactt acctttctat      60
ttcttaaata ggtcaattga tgagatagct gac                                  93

<210> SEQ ID NO 23
<211> LENGTH: 93
<212> TYPE: DNA
<213> ORGANISM: Sulfolobus solfataricus

<400> SEQUENCE: 23
tatctttacg aagccagctt tattgagagt accttgtatt ccctctttta tatcatgaat      60
aaacaagtca gctatctcat caattgacct att                                  93

<210> SEQ ID NO 24
<211> LENGTH: 93
<212> TYPE: DNA
<213> ORGANISM: Sulfolobus solfataricus

<400> SEQUENCE: 24
ctcaataaag ctggcttcgt aaagatagct gcaactgaac ctgggatcac aaaggatgtg      60
gagaaggtaa taagggctgc tgccatagca aac                                  93

<210> SEQ ID NO 25
<211> LENGTH: 93
<212> TYPE: DNA
<213> ORGANISM: Sulfolobus solfataricus

<400> SEQUENCE: 25
ttgctgttct aatccggtgt tattgtgagc gttagagtgg gtaattattg gtactttagt      60
ctctttgttt gctatggcag cagcccttat tac                                  93
```

```
<210> SEQ ID NO 26
<211> LENGTH: 93
<212> TYPE: DNA
<213> ORGANISM: Sulfolobus solfataricus

<400> SEQUENCE: 26
cacaataaca ccggattaga acagcaaaga atattgactg aagaaggtgt tgatccaggg    60
aaaatattaa taggtcattt aggtgataca gat                                 93

<210> SEQ ID NO 27
<211> LENGTH: 90
<212> TYPE: DNA
<213> ORGANISM: Sulfolobus solfataricus

<400> SEQUENCE: 27
aggaaaatga tctaatccaa taaaggatcc cttatctgct atcttcttta tgtaatctat    60
attatctgta tcacctaaat gacctattaa                                     90

<210> SEQ ID NO 28
<211> LENGTH: 99
<212> TYPE: DNA
<213> ORGANISM: Sulfolobus solfataricus

<400> SEQUENCE: 28
tcctttattg gattagatca ttttcctcat gatttatccc tacctgttga taagagaaat    60
gaaacgacct aagactaat caaagatggt tattcagat                            99

<210> SEQ ID NO 29
<211> LENGTH: 93
<212> TYPE: DNA
<213> ORGANISM: Sulfolobus solfataricus

<400> SEQUENCE: 29
tttatattct ggttttgcag ttccagcgtc gaatgtgcat aaataatcgt gagagatcat    60
tatcttatct gaataaccat ctttgattag tct                                 93

<210> SEQ ID NO 30
<211> LENGTH: 93
<212> TYPE: DNA
<213> ORGANISM: Sulfolobus solfataricus

<400> SEQUENCE: 30
gctggaactg caaaaccaga atataaacct aagcttgctc caagaattag tataactcta    60
atatttgagg atacgatacc gttcttaaag aga                                 93

<210> SEQ ID NO 31
<211> LENGTH: 109
<212> TYPE: DNA
<213> ORGANISM: Sulfolobus solfataricus

<400> SEQUENCE: 31
caacccgaat tcttagctga agaacttttt cggattttcc ttaaatattg tagctataac    60
ctcttcattc attcactcca tttctcttta agaacggtat cgtatcctc              109
```